US00H002213H

(19) United States

(12) Statutory Invention Registration

Oulmassov et al.

(10) Reg. No.: US H2213 H

(43) Published: Apr. 1, 2008

(54) ENHANCED PROTEINS AND METHODS FOR THEIR USE

(75) Inventors: Tim N. Oulmassov, Chesterfield, MO (US); William D. Rapp, St. Louis, MO (US); Kairong Tian, Wildwood, MO (US); Jason A. Wicker, Galveston, TX (US); William J. Welsh, Piscataway, NJ (US); Xia Wang, Wilmington, DE (US); Robert K. DeLisle, Monmouth Jct, NJ (US); Tyamagondlu V. Venkatesh, St. Louis, MO (US); Jihong Liang, Chesterfield, MO (US)

(73) Assignee: Monsanto Technology LLC, St. Louis, MO (US)

(21) Appl. No.: 10/409,993

(22) Filed: Apr. 9, 2003

(65) Prior Publication Data

US 2005/0079494 A1 Apr. 14, 2005

(51) Int. Cl.

*C12P 21/06* (2006.01)

(52) U.S. Cl. ..... 435/69.1

(58) Field of Classification Search ..... 435/69.1

See application file for complete search history.

*Primary Examiner*—Michelle Clement

(57) ABSTRACT

The present invention generally relates to the field of plant genetics and protein biochemistry. More specifically, the present invention relates to modified proteins having an increased number of essential amino acids. The present invention provides proteins modified to have an increased number of essential amino acids, nucleic acid sequences encoding the enhanced proteins, and methods of designing, producing, and using the same. The present invention also includes compositions, transformed host cells, transgenic plants, and seeds containing the enhanced proteins, and methods for preparing and using the same.

11 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ENHANCED PROTEINS AND METHODS FOR THEIR USE

The present invention generally relates to the field of plant genetics and protein biochemistry. More specifically, the present invention relates to modified proteins having an increased number of essential amino acids.

A full complement of amino acids is nutritionally important for all animals, as well as humans, and is often important to produce high quality livestock and animal products. However a typical animal diet can be deficient in one or more amino acids. For instance, essential amino acids, which limit protein utilization, are required by all animals for normal growth and development. Amino acid requirements vary from one animal species to the next. Typical essential amino acids include threonine, isoleucine, tryptophan, valine, arginine, lysine, methionine, and histidine.

Addition of essential amino acids to the diet of livestock can increase the commercial value of animals. The availability and absorption of sufficient nutrients is critical to an animal's production of commercially important products. The addition of essential amino acids to the diets of humans can prevent certain diseases caused by malnutrition or protein deficiency and promote normal growth and development.

Attempts have been made to modify animal diets to increase the amount of essential amino acids in the animal feed and human food (hereafter collectively referred to as food). For example, food is often supplemented with additional protein.

Genetic engineering techniques provide a more efficient approach to creating enhanced food containing increased amounts of essential amino acids. For example, essential amino acids may be substituted into a food protein in place of non-essential amino acids, thus increasing the nutritive value of that protein in the food. Furthermore, such an enhanced protein may be constitutively expressed in plants or seeds that are incorporated into food. Consequently, the enhanced protein will be present at relatively high levels in the food, providing significant nutritive improvement to the animal's diet.

Essential amino acids may be substituted in place of amino acids having similar characteristics in the native protein to assure that the overall three-dimensional structure of the protein is not compromised. For example, the amino acids may have similar hydrophobic or hydrophilic characteristics, resulting in similar hydrogen-binding, ionic, or van der Waals interactions. Thus, prediction of the potential position of amino acid substitution will be enhanced by a knowledge of the overall three-dimensional structure of the protein. The competent positions may be predicted from three-dimensional structures that are resolved experimentally (e.g., X-ray crystallography or NMR) or computationally built (e.g., using computers to construct homology models).

Clearly, there exists a need in the art for enhanced proteins that contain an increased amount of essential amino acids and methods for designing such proteins. Such proteins would significantly improve the nutritive value of animal feed, leading to improved quality and quantity of commercial animal products. Such proteins would also significantly improve the nutritive value of human food, leading to a decreased incidence of malnutrition and associated health problems and improving the overall growth and development of infants and children.

SUMMARY OF THE INVENTION

The present invention includes ad provides a modified polypeptide comprising a substitution of one or more amino acids selected from the group consisting of lysine, methionine, isoleucine and tryptophan into an unmodified polypeptide having an amino acid sequence of SEQ ID NO:1, preferably, wherein the modified polypeptide is capable of accumulating in a biological expression system, such as, for example, a seed. Preferably, the inventive modified polypeptide comprises greater than about 0.25% (weight per weight) increase of any one of the aforementioned amino acids, or any combination thereof, relative to SEQ ID NO: 1.

The present invention also includes and provides a seed from a transgenic plant containing, in the 5' to 3' direction, a heterologous promoter operably linked to a recombinant nucleic acid molecule encoding a modified glycinin polypeptide comprising a substitution of one or more amino acids selected from the group consisting of lysine, methionine, isoleucine and tryptophan into an unmodified glycinin polypeptide having an amino acid sequence of SEQ ID NO: 1, wherein said plant is an alfalfa, apple, banana, barley, bean, broccoli, cabbage, carrot, castorbean, celery, citrus, clover, coconut, coffee, corn, cotton, cucumber, Douglas fir, Eucalyptus, garlic, grape, linseed, Loblolly pine, melon, oat, olive, onion, palm, parsnip, pea, peanut, pepper, poplar, potato, radish, Radiata pine, rapeseed, rice, rye, sorghum, *Lupinus angustifolius,* Southern pine, soybean, spinach, strawberry, sugarbeet, sugarcane, sunflower, Sweetgum, tea, tobacco, tomato, turf, or wheat plant.

The present invention further includes and provides a plant from a seed from a transgenic plant containing, in the 5' to 3' direction, a heterologous promoter operably linked to a recombinant nucleic acid molecule encoding a modified glycinin polypeptide comprising a substitution of one or more essential amino acids selected from the group consisting of lysine, methionine, isoleucine and tryptophan into an unmodified glycinin polypeptide having an amino acid sequence of SEQ ID NO: 1, wherein said transgenic plant is an alfalfa, apple, banana, barley, bean, broccoli, cabbage, carrot, castorbean, celery, citrus, clover, coconut, coffee, corn, cotton, cucumber, Douglas fir, Eucalyptus, garlic, grape, linseed, Loblolly pine, melon, oat, olive, onion, palm, parsnip, pea, peanut, pepper, poplar, potato, radish, Radiata pine, rapeseed, rice, rye, sorghum, *Lupinus angustifolius,* Southern pine, soybean, spinach, strawberry, sugarbeet, sugarcane, sunflower, Sweetgum, tea, tobacco, tomato, turf, or wheat plant.

The present invention also includes and provides animal feed comprising a seed from a transgenic plant containing, in the 5' to 3' direction, a heterologous promoter operably linked to a recombinant nucleic acid molecule encoding a modified glycinin polypeptide comprising a substitution of one or more amino acids selected from the group consisting of lysine, methionine, isoleucine and tryptophan into an unmodified glycinin polypeptide having an amino acid sequence of SEQ ID NO: 1, wherein said plant is an alfalfa, apple, banana, barley, bean, broccoli, cabbage, carrot, castorbean, celery, citrus, clover, coconut, coffee, corn, cotton, cucumber, Douglas fir, Eucalyptus, garlic, grape, linseed, Loblolly pine, melon, oat, olive, onion, palm, parsnip, pea, peanut, pepper, poplar, potato, radish, Radiata pine, rapeseed, rice, rye, sorghum, *Lupinus angustifolius,* Southern pine, soybean, spinach, strawberry, sugarbeet, sugarcane, sunflower, Sweetgum, tea, tobacco, tomato, turf, or wheat plant.

The present invention includes and provides animal feed comprising a transgenic plant containing, in the 5' to 3' direction, a heterologous promoter operably linked to a recombinant nucleic acid molecule encoding a modified glycinin polypeptide comprising a substitution of one or more essential amino acids selected from the group consisting of lysine, methionine, isoleucine and tryptophan into an unmodified glycinin polypeptide having an amino acid sequence of SEQ ID NO: 1, wherein said plant is an alfalfa, apple, banana, barley, bean, broccoli, cabbage, carrot, castorbean, celery, citrus, clover, coconut, coffee, corn, cotton, cucumber, Douglas fir, Eucalyptuus, garlic, grape, linseed, Loblolly pine, melon, oat, olive, onion, palm, parsnip, pea, peanut, pepper, poplar, potato, radish, Radiata pine, rapeseed, rice, rye, sorghum, *Lupinus augustifolis,* Southern pine, soybean, spinach, strawberry, sugarbeet, sugarcane, sunflower, Sweetgum, tea, tobacco, tomato, turf, or wheat plant.

BRIEF DESCRIPTION OF THE SEQUENCES

Figure 1:
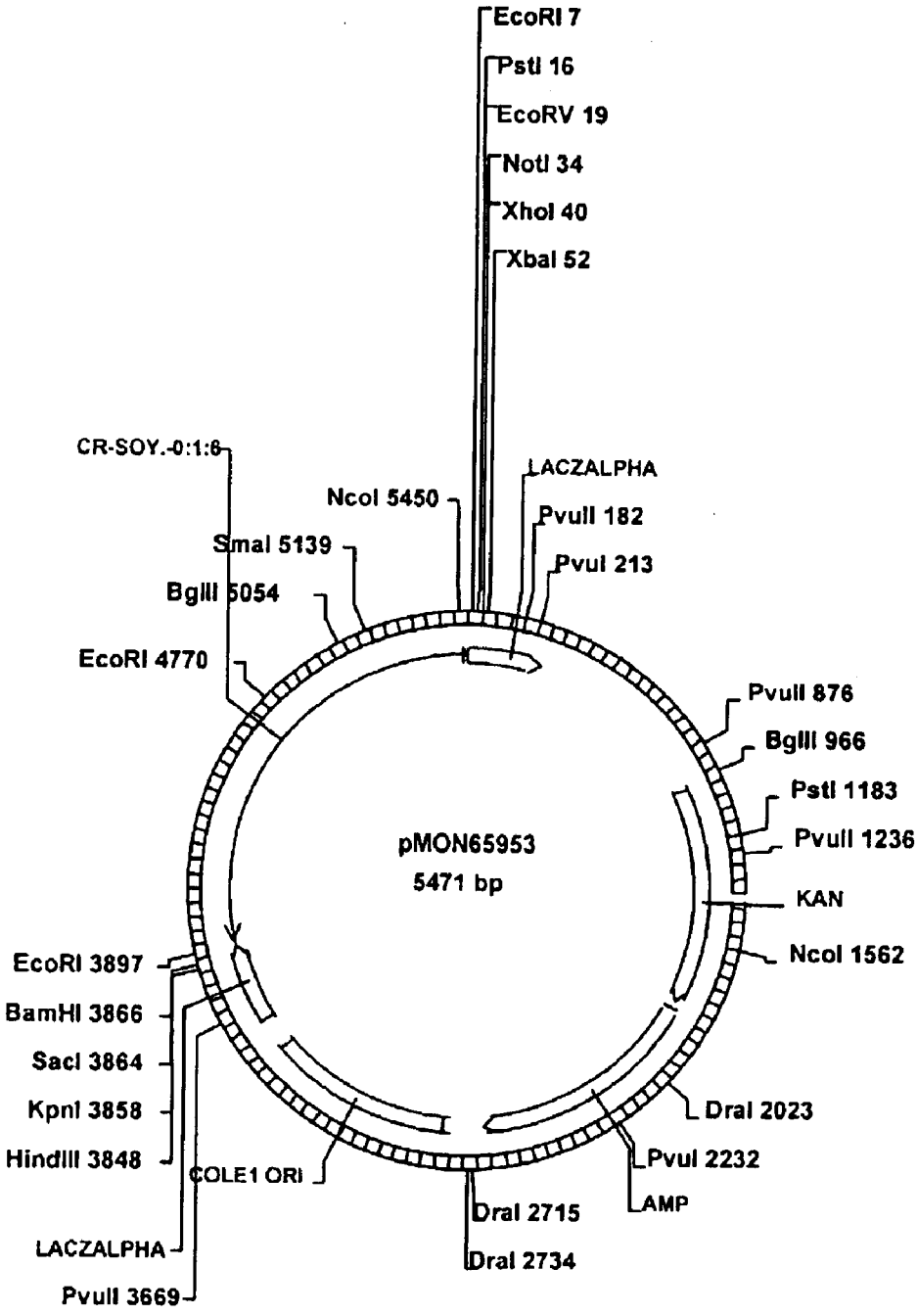
FIG. 1 is a plasmid map of pMON65953.

SEQ ID NO: 1 is a *Glycine max* glycinin amino acid sequence [with 1–9 N-terminus and 471–476 C-terminus].

SEQ ID NO: 2 is a *Glycine max* glycinin cDNA sequence.

SEQ ID NO: 3 is an oligonucleotide primer.

SEQ ID NO: 4 is an oligonucleotide primer.

SEQ ID NO: 5 is a FLAG epitope amino acid sequence.

SEQ ID NO: 6 is a DNA sequence encoding the FLAG epitope amino acid sequence of SEQ ID NO: 5.

SEQ ID NO: 7 is an oligonucleotide primer.

SEQ ID NO: 8 is an oligonucleotide primer.

SEQ ID NO: 9 is an amino-terminal epitope (FLAG)-tagged form of SEQ ID NO: 1.

SEQ ID NO: 10 is a DNA sequence encoding the amino-terminal epitope (FLAG)-tagged SEQ ID NO: 9.

SEQ ID NO: 11 is an oligonucleotide primer.

SEQ ID NO: 12 is an oligonucleotide primer.

SEQ ID NO: 13 is a carboxy-terminal epitope (FLAG)-tagged form of SEQ ID NO: 1.

SEQ ID NO: 14 is a DNA sequence encoding the carboxy-terminal epitope (FLAG)-tagged SEQ ID NO: 13.

SEQ ID NO: 15 is a mature form of a modified glycinin amino acid sequence.

SEQ ID NO: 16 is a DNA encoding SEQ ID NO: 15.

SEQ ID NOs: 17 through 54 are oligonucleotide primers.

DEFINITIONS

The following definitions are provided as an air to understanding the detailed description of the present invention.

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence. "Percent identity" is the identity fraction times 100.

The phrase "essential amino acids" refer to amino acids that an organism itself is unable to synthesize and which the organism therefore must obtain through the organism's diet. Essential amino acids vary among different animals depending on the animal species, and may include one or more of the group of amino acids threonine, isoleucine, tryptophan, valine, arginine, lysine, methionine, histidine, leucine, and phenylalanine.

The phrase "antigenic epitope" refers to any discrete segment of a molecule, protein, or nucleic acid capable of eliciting an immune response, where the immune response results in the production of antibodies reactive with the antigenic epitope.

The phrases "coding sequence", "open reading frame", "structural sequence", and "structural nucleic acid sequence" refer to a physical structure comprising an orderly arrangement of nucleic acids. The nucleic acids are arranged in a series of nucleic acid triplets that each form a codon. Each codon encodes for a specific amino acid. Thus the coding sequence, structural sequence, and structural nucleic acid sequence encode a series of amino acids forming a protein, polypeptide, or peptide sequence. The coding sequence, structural sequence, and structural nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The phrases "DNA sequence", "nucleic acid sequence", and "nucleic acid molecule" refer to a physical structure comprising an orderly arrangement of nucleic acids. The DNA sequence or nucleic acid sequence may be contained within a larger nucleic acid molecule, vector, or the like. In addition, the orderly arrangement of nucleic acids in these sequences may be depicted in the form of a sequence listing, figure, table, electronic medium, or the like.

The term "expression" refers to the transcription of a gene to produce the corresponding mRNA and translation of this mRNA to produce the corresponding gene product (i.e., a peptide, polypeptide, or protein).

The term "expression of antisense RNA" refers to the transcription of a DNA to produce a first RNA molecule capable of hybridizing to a second RNA molecule.

The term "gene" refers to chromosomal DNA, plasmid DNA, cDNA, synthetic DNA, or other DNA that encodes a peptide, polypeptiide, protein, or RNA molecule.

The term "homology" refers to the level of similarity between two or more nucleic acid or amino acid sequences in terms of percent of positional identity (i.e., sequence similarity or identity).

The term "heterologous" refers to the relationship between two or more nucleic acid or protein sequences that are derived from different sources. For example, a promoter is heterologous with respect to a coding sequence if such a combination is not normally found in nature. In addition, a particular sequence may be "heterologous" with respect to a cell or organism into which it is inserted (i.e., does not naturally occur in that particular cell or organism).

The term "hybridization" refers to the ability of a strand of nucleic acid to join with a complementary strand via base pairing. Hybridization occurs when complementary nucleic acid sequences in the two nucleic acid strands contact one another under appropriate conditions.

The phrase "nucleic" refers to deoxyribonucleic acid (DNA) and ribonucleic acid (RNA).

The term "phenotype" refers to traits exhibited by an organism resulting from the interaction of genotype and environment.

The phrases "polyadenylation signal" or "polyA signal" refers to a nucleic acid sequence located 3' to a coding region that promotes the addition of adenylate nucleotides to the 3' end of the mRNA transcribed from the coding region.

The phrase "operably linked" refers to the functional spatial arrangement of two or more nucleic acid regions of nucleic acid sequences. For example, a promoter region may be positioned relative to a nucleic acid sequence such that transcription of the nucleic acid sequence is directed by the promoter region. Thus, a promoter region is "operably linked" to the nucleic acid sequence.

The term/phrase "promoter" or "promoter region" refers to a nucleic acid sequence, usually found upstream (5') to a coding sequence, that directs transcription of the nucleic acid sequence into mRNA. The promoter or promoter region typically provide a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, etc. The activity or strength or a promoter may be measured in terms of the amounts of RNA it produces, or the amount of protein accumulation in a cell or tissue, relative to a promoter whose transcriptional activity has been previously assessed.

The phrases "recombinant nucleic acid vector" and "recombinant vector" refer to any agent such as a plasmid, cosmid, virus, autonomously replicating sequence, phage, or linear single-stranded, circular single-stranded, linear double-stranded, or circular double-stranded DNA or RNA nucleotide sequence. The recombinant vector may be derived from any source; is capable of genomic integration or autonomous replication; and comprises a promoter nucleic acid sequence operably linked to one or more nucleic acid sequences. A recombinant vector is typically used to introduce such operably linked sequences into a suitable host.

The term "regeneration" refers to the process of growing a plant from a plant cell or plant tissue (e.g., plant protoplast or explant).

The phrase "selectable marker" refers to a nucleic acid sequence whose expression confers a phenotype facilitating identification of cells containing the nucleic acid sequence. Selectable markers include those which confer resistance to toxic chemicals (e.g., ampicillin resistance, kanamycin resistance), complement a nutritional deficiency (e.g., uracil, histidine, leucine), or impart a visually distinguishing characteristic (e.g., color changes or fluorescence).

The term "transcription" refers to the process of producing an RNA copy from a DNA template.

The term "transgenic" refers to organisms into which exogenous nucleic acid sequences are integrated.

The term "vector" refers to a plasmid, cosmid, bacteriophage, or virus that carries exogenous DNA into a host organism.

The phrase "regulatory sequence" refers to a nucleotide sequence located upstream (5'), within, or a downstream (3') to a coding sequence. Transcription and expression of the coding sequence is typically impacted by the presence or absence of the regulatory sequence.

The phrase "substantially homologous" refers to two sequences which are at least 90% identical in sequence, as measured by the BestFit program described herein (Version 10; Genetics Computer Groups, Inc., University of Wisconsin Biotechnology Center, Madison, Wis.), using default parameters.

The term "transformation" refers to the introduction of nucleic acid into a recipient host. The term "host" refers to bacteria cells, fungi, animals or animal cells, plants or seeds, or any plant parts or tissues including protoplasts, calli, roots, tubers, seeds, stems, leaves, seedlings, embryos, and pollen.

As used herein, the phrase "transgenic plant" refers to a plant where an introduced nucleic acid is stably introduced into a genome of the plant, for example, the nuclear or plasmid genomes.

As used herein, the phrase "substantially purified" refers to a molecule separated from substantially all other molecules normally associated with it in its native state. More preferably a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The phrase "substantially purified" is not intended to encompass molecules present in their native state.

DETAILED DESCRIPTION OF THE PREFERRED EMBODIMENTS

The present invention includes and provides modified polypeptides having increased levels of essential amino acids, and methods for their use, design, and production. The modified polypeptides are characterized by improved nutritional content relative to the unmodified polypeptide from which they are engineered.

Polypeptide Sequences

The present invention includes and provides a modified polypeptide having increased levels of essential amino acids. The modified polypeptide is characterized in having improved nutritional content relative to the unmodified polypeptide. The modified polypeptide generally comprises an addition or substitution of at least one essential amino acid into the amino acid sequence of the unmodified polypeptide. Such essential amino acids are preferably selected from the group consisting of threonine, isoleucine, tryptophan, valine, arginine, lysine, methionine, and histidine. In a preferred embodiment, the modified polypeptide generally comprises a substitution of at least one essential amino acid into the amino acid sequence of the unmodified polypeptide. In a more preferred embodiment, the modified polypeptide generally comprises a substitution of at least one isoleucine residue in the amino acid sequence of the unmodified polypeptide.

As used herein, a "substitution" of an amino acid means the replacement of an amino acid in a protein with a different amino acid. A "substitution" does not therefore change the total number of amino acids in the modified protein. In a preferred embodiment, the modified polypeptide is capable of accumulating in a cell. In another preferred embodiment, the modified polypeptide is capable of accumulating in a seed. As used herein, "accumulates in a seed" or "cell" means the polypeptide is generated and maintained at a rate greater than the rate of degradation in the seed or cell. In yet another preferred embodiment, the modified polypeptide is capable of forming timers. As used herein, a protein is "capable of forming trimers" when the protein is able to self-assemble and trimerize when translated in a cellular environment. In a preferred embodiment, the level of trimerization of the modified polypeptide is 10% of the level of trimerization of the unmodified polypeptide, and more preferably 20%, 30%, 40%, 50%, 60%, 70%, 80%, 90%, 95%, and 99% of the level of trimerization of the unmodified polypeptide as determined in Example 3, below.

The modified polypeptide may generally be any polypeptide that is suitable for incorporation into the diet of an animal. The polypeptide is preferably selected from the group of polypeptides that are expressed at relatively high concentrations in a given plant tissue, such as seed storage proteins, vegetative storage proteins, enzymes, or structural proteins. The modified polypeptide is more preferably a modified glycinin, 7S storage globulin, 11S storage globulin, albumin, prolamin, arcelin, or leghemoglobin polypeptide.

In one embodiment of the present invention, the modified polypeptide has lysine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has methionine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has threonine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has valine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has arginine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In another embodiment of the present invention, the modified polypeptide has histidine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In a preferred embodiment of the present invention, the modified polypeptide has tryptophan residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In a preferred embodiment of the present invention, the modified polypeptide has isoleucine residues substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In a more preferred aspect, the modified polypeptide is a glycinin polypeptide (SEQ ID NO: 1) having the essential amino acid tryptophan substituted in place of at least 1, and more preferably in place of at least 2, 3, 4, 5, 6, 7, 8, 9, 10, 11, 12, 13, 14, 15, 16, 17, 18, 19, 20, 21, or 22 of the amino acids selected from the group consisting of [target group], with respect to the unmodified glycinin sequence (SEQ ID NO: 1).

The modified polypeptide is preferably a glycinin polypeptide (SEQ ID NO: 1) having the essential amino acid isoleucine substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 of the amino acids selected from the group consisting of L20, L152, L366, L122, L333, L345, L17, L32, L371, L50, L328, L387, L55, L302, L338, L60, L174, L336, L393, L464, L165, L202, L207, L210, L433, L243, L426, L432, L436, F81, F117, Y134, F330, F351, Y364, F410, Y412, and F463 with respect to the unmodified glycinin sequence (SEQ ID NO: 1).

In a preferred embodiment, the modified polypeptide is further modified to have an increased content of at least 1, and more preferably 2, 3, or 4 of the essential amino acids selected from the group consisting of histidine, lysine, methionine, and phenylalanine. Other amino acid substitutions may also be made, as needed, for structural and nutritive enhancement of the polypeptide.

In another preferred embodiment of the present invention, the modified glycinin polypeptide has the essential amino acid tryptophan substituted in place of at least 1, and more preferably in place of at least 2, 3, 4, 5, 6, 7, 8, 9, 10, 11, 12, 13, 14, 15, 16, 17, 18, 19, 20, 21, or 22 of the amino acids selected from the group consisting of [group] and the essential amino acid isoleucine substituted in place of at least 1, and preferably in place of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38 of the amino acids selected from the group consisting of L20, L152, L366, L122, L333, L345, L17, L32, L371, L50, L328, L387, L55, L302, L338, L60, L174, L336, L393, L464, L165, L202, L207, L210, L433, L243, L426, L432, L436, F81, F117, Y134, F330, F351, Y364, F410, Y412, and F463 with respect to the unmodified glycinin sequence (SEQ ID NO: 1).

In a preferred aspect, the modified glycinin polypeptide includes one or more essential amino acid substitutions relative to the unmodified glycinin polypeptide. In an even more preferred aspect, the modified glycinin polypeptide includes two or more essential amino acid substitutions, where the essential amino acids are both tryptophan and isoleucine. In a preferred aspect, the modified polypeptide has at least 1, more preferably 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 51, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, and 106 tryptophan or isoleucine substitutions, in any combination, where the tryptophan substitutions are one or more of [group], and the isoleucine substitutions are one or more of L20, L152, L366, L122, L133, L345, L17, L32, L371, L50, L328, L387, L55, L302, L338, L60, L174, L336, L393, L464, L165, L202, L207, L210, L433, L243, L426, L432, L436, F81, F117, Y134, F330, F351, Y364, F410, Y412, and F463.

The modified polypeptide may be further modified to provide additional desirable features. For example the modified polypeptide may be further modified to increase the content of other essential amino acids, enhance translation of the amino acid sequence, alter post-translational modifications (e.g., phosphorylation of glycosylation sites), transport the polypeptide to a compartment inside or outside of the cell, insert or delete cell signaling motifs, etc.

In another embodiment of the present invention, the modified polypeptide has one or more, two or more, or three or more of the amino acid residues selected from the group consisting of isoleucine, lysine, methionine, threonine, tryptophan, valine, arginine, and histidine, substituted in place of at least 1, and more preferably in place of at least 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids relative to the unmodified polypeptide.

In a preferred embodiment, a modified protein comprises an increase of greater than 0.25%, greater than 0.5%, greater than 1%, greater than 2%, greater than 3%, greater than 5%, greater than 7%, greater than 10%, greater than 15%, or greater than 20% (weight per weight) of threonine, isoleucine, tryptophan, valine, or arginine, or any combination thereof, relative to the unmodified polypeptide.

In a preferred embodiment, a modified glycinin polypeptide comprises an increase of greater than 0.25%, greater than 0.5%, greater than 1%, greater than 2%, greater than 3%, greater than 5%, greater than 7%, greater than 10%, greater than 15, or greater than 20% (weight per weight) of threonine, isoleucine, tryptophan, valine, or arginine, or any combination thereof, relative to the unmodified glycinin polypeptide.

Nucleic Acid Molecules

The present invention includes and provides a recombinant nucleic acid molecule encoding a modified polypeptide of the present invention having increased levels of essential amino acids.

Nucleic acid hybridization is a technique well known to those of skill in the art of DNA manipulation. The hybridization properties of given pair of nucleic acids is an indication of their similarity or identity.

The nucleic acid molecules preferably hybridize, under low, moderate, or high stringency conditions, with any of the nucleic acid sequences of the present invention.

The hybridization conditions typically involve nucleic acid hybridization in about 0.1X to about 10X SSC (diluted from a 20X SSC stock solution containing 3 M sodium chloride and 0.3 M sodium citrate, pH 7.0 in distilled water), about 2.5X to about 5X Denhardt's solution (diluted from a 50X stock solution containing 1% (w.v) bovine serum albumin, 1% (w/v)ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 20° C. to about 70° C. for several hours to overnight. The hybridization conditions are preferably provided by 6X SSC, 5X Denhardt's solution, 100mg/mL fish sperm DNA, and 0.1% (w/v) SDS, with an incubation at 55° C. for several hours.

The hybridization is generally followed by several wash steps. The wash compositions generally comprise 0.1X to about 10X SSC, and 0.01% (w/v) to about 0.5% (w/v) SDS with a 15 minute incubation at about 20° C. to about 70° C. Preferably, the nucleic acid segments remain hybridized after washing at least one time in 0.1X SSC at 65° C. For example, the salt concentration in the wash step can be selected from a low stringency of about 2X SSC at 50° C. to a high stringency of about 0.2X SSC at 65° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Low stringency conditions may be used to select nucleic acid sequences with lower sequence identities to a target nucleic acid sequence. One may wish to employ conditions such as about 6X SSC to about 10X SSC, at temperatures ranging from about 20° C. to about 55° C., and preferably a nucleic acid molecule will hybridize to one or more nucleic acid molecules of the present invention under low stringency conditions of about 6X SSC and about 45° C. In a preferred embodiment, a nucleic acid molecule will hybridize to one or more nucleic acid molecules of the present invention under moderately stringent conditions, for example at about 2X SSC and about 65° C. In a particularly preferred embodiment, a nucleic acid molecule of the present invention will hybridize to one or more of the above-described nucleic acid molecules under high stringency conditions such as 0.2X SSC and about 65° C.

A nucleic acid sequence of the present invention preferably hybridizes with a complementary nucleic acid sequence encoding any of the polypeptides described herein, the complement thereof, or any fragments thereof.

A nucleic acid sequence of the present invention preferably hybridized under low stringency conditions with a complementary nucleic acid sequence encoding any of the polypeptides described herein, the complement thereof, or any fragments thereof.

A nucleic acid sequence of the present invention preferably hybridizes under high stringency conditions with a complementary nucleic acid sequence encoding any of the polypeptides described herein, the complement thereof, or any fragments thereof.

The percent of sequence identity is preferably determined using the "Best Fit" or "Gap" program of the Sequence Analysis Software Package™ (Version 10: Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, 1981; Smith et al., 1983). The percent identity is most preferably determined using the "Best Fit" program using default parameters.

In an embodiment, the fragments are between 3000 and 1000 consecutive nucleotides, 1800 and 150 consecutive nucleotides, 1500 and 500 consecutive nucleotides, 1300 and 250 consecutive nucleotides, 1000 and 200 consecutive nucleotides, 800 and 150 consecutive nucleotides, 500 and 100 consecutive nucleotides, 300 and 75 consecutive nucleotides, 100 and 50 consecutive nucleotides, 50 and 25 consecutive nucleotides, or 20 and 10 consecutive nucleotides long of a nucleic molecule of the present invention.

In another embodiment, the fragment comprises at least 20, 30, 40, or 50 consecutive nucleotides of a nucleic acid sequence of the present invention.

Promoters

In a preferred embodiment any of the disclosed nucleic acid molecules may be operably linked to a promoter. In a particularly preferred embodiment, the promoter is selected from the group consisting of a 11S or legumin-type promoter (e.g., soybean glycinin promoters), a USP Vicia faba promoter and a 7S or vicilin-type promoters. In an embodiment, the promoter is tissue specific, preferably seed specific.

In one aspect, a promoter is considered tissue or organ specific if the level of an mRNA in that tissue or organ is expressed at a level that is at least 10 fold higher, preferably at least 100 fold higher, or at least 1,000 fold higher than another tissue or organ. The level of mRNA can be measure either at a single time point or at multiple time points and as such the fold increase can be average fold increase or an extrapolated value derived from experimentally measured values. As it is a comparison of levels, any method that measures mRNA levels can be used. In a preferred aspect, the tissue or organs compared are a seed or seed tissue with a leaf or leaf tissue. In another preferred aspect, multiple tissues or organs are compared. A preferred multiple comparison is a seed or seed tissue compared with two, three, four, or more tissues or organs selected from the group consisting of floral tissue, floral apex, pollen, leaf, embryo, shoot, leaf primodia, shoot apex, root, root tip, vascular tissue and cotyledon. As used herein, examples of plant organs are seed, leaf, root, etc. and example of tissues are leaf primodia, shoot apex, vascular tissue, etc.

The activity or strength of a promoter may be measured in terms of the amount of mRNA or protein accumulation it specifically produces, relative to the total amount of mRNA or protein. The promoter preferably expresses an operably linked nucleic acid sequence at a level greater than 2.5%; more preferably greater than 5%, 6%, 7%, 8%, or 9%; even more preferably greater than 10%, 11%, 12%, 13%, 14%, 15%, 16%, 17%, 18%, or 19%; and most preferably greater than 20% of the total mRNA.

Alternatively, the activity or strength of a promoter may be expressed relative to a well-characterized promoter (for which transcriptional activity was previously assessed). For example, a promoter of interest may be operably linked to a reporter sequence (e.g., GUS) and introduced into a specific cell type. A known promoter may be similarly prepared and introduced into the same cellular context. Transcriptional activity of the promoter of interest is then determined by comparing the amount of reporter expression, relative to the known promoter. The cellular context is preferably soybean. Activity or strength of a promoter may be measured in terms of the amount of mRNA or protein accumulation it specifically produces, relative to the total amount of mRNA or protein. A promoter preferably expresses an operably linked nucleic acid sequence at a level greater than 2.5%; more preferably greater than 5%, 6%, 7%, 8%, or 9%; even more preferably greater than 10%, 11%, 12%, 13%, 14%, 15%, 16%, 17%, 18%, or 19%; and most preferably greater than 20% of the total mRNA.

Alternatively, the activity or strength of a promoter may be expressed relative to a well-characterized promoter (for which transcriptional activity was previously assessed). For example, a promoter of interest may be operably linked to a reported sequence (e.g., GUS) and introduced into a specific cell type. A known promoter may be similarly prepared and introduced into the same cellular context. Transcriptional activity of the promoter of interest is then determined by comparing the amount of reporter expression, relative to the known promoter. The cellular context is preferably soybean.

Modified Structural Nucleic Acid Sequences

The nucleic acids of the present invention may also be operably linked to a modified structural nucleic acid sequence that is heterologous with respect to the nucleic acids of the present invention. The structural nucleic acid sequence may be modified to provide various desirable features. For example, a structural nucleic acid sequence may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

Codon Usage in Nucleic Acid Sequences

Due to the degeneracy of the genetic code, different nucleotide codons may be used to code or particular amino acid. A host cell often displays a preferred pattern of codon usage. Structural nucleic acid sequences are preferably constructed to utilize the codon usage pattern of the particular host cell. This generally enhances the expression of the structural nucleic acid sequence in a transformed host cell. Any of the above described nucleic acid and amino acid sequences may be modified to reflect the preferred codon usage of a host cell or organism in which they are contained. Modification of a structural nucleic acid sequence for optimal codon usage in plants is described in U.S. Pat. No. 5,689,052.

Other Modification of Structural Nucleic Acid Sequences

Additional variations in the structural nucleic acid sequences described above may encode proteins having equivalent or superior characteristics when compared to the proteins from which they are engineered. Mutations may include deletions, insertions, truncations, substitutions, fusions, shuffling or motif sequences, and the like.

Mutations to a structural nucleic acid sequence may be introduced in either a specific or random manner, both of which are well known to those of skill in the art of molecular biology. A myriad of site-directed mutagenesis techniques exist, typically using oligonucleotides to introduce mutations at specific locations in a structural nucleic acid sequence. Examples include single strand rescue (Kunkel et al., 1985), unique site elimination (Deng and Nicklofd, 1992), nick protection (Vandeyar et al., 1988), and PCR (Costa et al., 1996). Random or non-specific mutations may be generated by chemical agents (for a general review, see Singer and Kusmierek, 1982) such as nitrosoguanidine (Cerda-Olmedo et al., 1968; Guerola et al., 1971); 2-aminopurine (Rogan and Bessman, 1970); or by biological methods such as passage through mutator strains (Greener et al., 1997).

Modifications to a nucleic acid sequence may or may not result in changes in the amino acid sequence. Changes that, because of the degeneracy of the genetic code, do not affect the amino acid encoded by the changed codon can occur. In a preferred embodiment, the nucleic acid encoding the modified protein has between 5 and 500 of these changes, more preferably between 10 and 300 changes, even more preferably between 25 and 150 changes, and most preferably between 1 and 25 changes. In a further preferred embodiment, nucleic acid molecules of the present invention include nucleic acid molecules that have 80%, 85%, 90%, 95%, or 99% sequence identity with nucleic acid molecules modified in this way. In a further preferred embodiment, nucleic acid molecules of the present invention include nucleic acid molecules that hybridize to nucleic acid molecules modified in this way, as well as nucleic acid molecules that hybridize under low or high stringency conditions to nucleic acid molecules modified in this way.

A second type of change includes additions, deletions, and substitutions in the nucleic acid sequence which result in an altered amino acid sequence. In a preferred embodiment, the nucleic acid encoding the modified protein has between 5 and 500 of these nucleic acid changes, more preferably between 10 and 300 changes, even more preferably between 25 and 150 changes, and most preferably between 1 and 25 of these changes. In a further preferred embodiment, nucleic acid molecules of the present invention include nucleic acid molecules that have 80%, 85%, 90%, 95%, or 99% sequence identity with nucleic acid molecules modified in this way. In a further preferred embodiment, nucleic acid molecules of the present invention include nucleic acid molecules that hybridize to nucleic acid molecules modified in this way, as well as nucleic acid molecules that hybridize under low or high stringency conditions to nucleic acid molecules modified in this way.

Additional methods of making the alterations described above are described by Ausubel et al. (1995); Bauer et al. (1985); Frits Eckstein et al. (1982); Sambrook et al. (1989); Smith et al. (1981); and Osuna et al. (1994).

Modifications may be made to the protein sequences described herein and the nucleic acid sequences which encode them that maintain the desired properties of the molecule. The following is a discussion based upon changing the amino acid sequence of a protein to create an equivalent, or possibly an improved, second-generation molecule. The amino acid changes may be achieved by changing the codons of the structural nucleic acid sequence, according to the codons given in Table 1.

TABLE 1

Codon degeneracy of amino acids

| Amino acid | One letter | Three letter | Codons |
|---|---|---|---|
| Alanine | A | Ala | GCA GCC GCG GCT |
| Cysteine | C | Cys | TGC TGT |
| Aspartic acid | D | Asp | GAC GAT |
| Glutamic acid | E | Glu | GAA GCG |
| Phenylalanine | F | Phe | TTC TTT |
| Glycine | G | Gly | GGA GGC GGG GGT |
| Histidine | H | His | CAC CAT |
| Isoleucine | I | Ile | ATA ATC ATT |
| Lysine | K | Lys | AAA AAG |
| Leucine | L | Leu | TTA TTG CTA CTC CTG CTT |
| Methionine | M | Met | ATG |
| Asparagine | N | Asn | AAC AAT |
| Proline | P | Pro | CCA CCC CCG CCT |
| Glutamine | Q | Gln | CAA CAG |
| Arginine | R | Arg | AGA AGG CGA CGC CGG CGT |
| Serine | S | Ser | AGC AGT TCA TCC TCG TCT |
| Threonine | T | Thr | ACA ACC ACG ACT |
| Valine | V | Val | GTA GTC GTG GTT |
| Tryptophan | W | Trp | TGG |
| Tyrosine | Y | Tyr | TAC TAT |

Certain amino acids may be substituted for other amino acids in a protein sequence without appreciate loss of the desired activity. It is thus contemplated that various changes may be made in the peptide sequences of the disclosed protein sequences, or their corresponding nucleic acid sequences without appreciable loss of the biological activity.

In making such changes, the hydropathic index of amino acids may be considered. The importance of the hydropathic amino acid index in conferring interactive biological function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics. These are: isoleucine (+4.5); valine (+4.2); leucine (+3.8); phenylaline (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

It is also understood in the art that the substitution of like amino acids may be made effectively on the basis of hydrophilicity. U.S. Pat. No. 4,554,101 (Hopp, issued Nov. 19, 1985) states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (±2.0±1); serine (±0.3); asparagine/glutamine (±0.2); glycine (0); threonine (−0.4); proline (−0.5±1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within ±2 is preferred, those within ±1 are more preferred, and those within ±0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine. Changes which are not expected to be advantages may also be used if these resulted proteins have improved rumen resistance and increased resistance to proteolytic degradation, or both improved rumen resistance and increased resistance to proteolytic degradation, relative to the unmodified polypeptide from which they are engineered.

Recombinant Vectors

Any of the promoters and structural nucleic acid sequences described above may be provided in a recombinant vector. A recombinant vector typically comprises, in a 5' to 3' orientation: a promoter to direct the transcription of a structural nucleic acid sequence and a structural nucleic acid sequence. Suitable promoters and structural nucleic acid sequences are described herein. The recombinant vector may further comprise a 3' transcriptional terminator, a 3' polyadenylation signal, other untranslated nucleic acid sequences, transit and targeting nucleic acid sequences, selectable markers, enhancers, and operators, as desired.

Means for preparing recombinant vectors are well known in the art. Methods for making recombinant vectors particularly suited to plant transformation are described in U.S. Pat. Nos. 4,791,908; 4,940,835; 4,769,061; and 4,757,011. These types of vectors have also been reviewed (Rodriguez et al., 1988; Glick et al., 1993).

Typical vectors useful for expression of nucleic acids in higher plants are well known in the art and include vectors derived from the tumor-inducing (Ti) plasmid of *Agrobacterium tumefaciens* (Rogers et al., 1987). Other recombinant vectors useful for plant transformation, including the pCaMVCN transfer control vector, have also been described (Fromm et al., 1985).

Additional Promoters in the Recombinant Vector

One or more additional promoters may also be provided in the recombinant vector. These promoters may be operably linked, for example, without limitation, to any of the structural nucleic acid sequences described above. Alternatively, the promoters may be operably linked to other nucleic acid sequences, such as those encoding transit peptides, selectable marker proteins, or antisense sequences.

These additional promoters may be selected on the basis of the cell type into which the vector will be inserted. Also, promoters which function in bacteria, yeast, and plants are all well taught in the art. The additional promoters may also be selected on the basis of their regulatory features. Examples of such features include enhancement of transcriptional activity, inducibility, tissue specificity, and developmental stage-specificity. In plants, promoters that are inducible, or viral or synthetic origin, constitutively active, temporally regulated, and spatially regulated have been described (Poszkowski et al., 1989; Odell et al., 1985; Chau et al., 1989).

Often-used constitutive promoters include the CaMV 35S promoter (Odell et al., 1985), the enhanced CaMV 35S promoter, the Figwort Mosaic Virus (FMV) promoter (Richins et al., 1987), the mannopine synthase (mas) promoter, the nopaline synthase (nos) promoter, and the octopine synthase (ocs) promoter.

Useful inducible promoters include promoters induced by salicylic acid or polyacrylic acids (PR-1; Williams et al., 1992), induced by application of safeners (substituted benzenesulfonamide herbicides; Hershey and Stoner, 1991), heat-shock promoters (Ou-Lee et al., 1986; Ainley et al., 1990), a nitrate-inducible promoter derived from the spinach nitrite reductase structural nucleic acid sequence (Back et al., 1991), hormone-inducible promoters (Yamaguchi-Shinozaki et al., 1990; Kares et al., 1990), and light-inducible promoters associated with the small subunit of RuBP carboxylase and LHCP families (Kuhlemeier et al., 1989; Feinbaum et al., 1991; Weisshaar et al., 1991; Lam and Chua, 1990; Castresana et al., 1988; Schulze-Lefert et al., 1989).

Examples of useful tissue or organ specific promoters include β-conglycinin, (Doyle et al., 1986; Slighton and Beachy, 1987), and other seed specific promoters (Knutzon et al., 1992; Bustos et al., 1991; Lam and Chua, 1991). Plant functional promoters useful for preferential expression in seeds include those from plant storage proteins and from proteins involved in fatty acid biosynthesis in oilseeds. Examples of such promoters include the 5' regulatory regions from such structural nucleic acid sequences as napin (Kridl et al., 1991), phaseolin, zein, soybean trypsin inhibitor, ACP, stearoyl-ACP desaturase, and oleosin. Seed-specific regulation is further discussed in European Application EP 0 255 378.

Another exemplary seed specific promoter is a lectin promoter. The lectin protein in soybean seeds is encoded by a single structural nucleic acid sequence (Le1) that is only expressed during seed maturation. A lectin structural nucleic acid sequence and seed-specific promoter have been characterized and used to direct seed specific expression in transgenic tobacco plants (Vodkin et al., 1983; Lindstrom et al., 1990).

Particularly preferred additional promoters in the recombinant vector include the nopaline synthase (nos), mannopine synthase (mas), and octopine synthase (ocs) promoters, which are carried on tumor-inducing plasmids of *Agrobacterium tumefaciens;* the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-biphosphate carboxylase (ssRUBISCO); the EIF-4A promoter from tobacco (Mandel et al., 1995); corn sucrose synthetase 1 (Yang and Russell, 1990); corn alcohol dehydrogenase 1 (Vogel et al., 1989); corn light harvesting complex (Simpson, 1986); corn heat shock protein (Odell et al., 1985); the chitinase promoter from *Arabidopsis* (Samac et al., 1991); the LTP (Lipid Transfer Protein) promoters from broccoli (Pyee et al., 1995); petunia chalcone isomerase (Van Tunen et al., 1988); bean glycine rich protein 1 (Keller et al., 1989); potato patatin (Wenzler et al., 1989); the ubiquitin promoter from maize (Christensen et al., 1992); and the actin promoter from rice (McElroy et al., 1990).

An additional promoter is preferably seed selective, tissue selective, constitutive, or inducible. The promoter is most preferably the nopaline synthase (nos), octopine synthase (ocs), mannopine synthase (mas), cauliflower mosaic virus 19S and 35S (CaMV19S), CaMV35S), enhanced CaMV (eCaMV), ribulose 1,5-biphosphate carboxylase (ssRUBISCO), figwort mosaic virus (FMV), CaMV derived AS4, tobacco RB7, wheat POX1, tobacco EIF-4, lectin protein (Le1), or rice RC2 promoter.

Recombinant Vectors Having Additional Structural Nucleic Acid Sequences

A recombinant vector may also contain one or more additional structural nucleic acid sequences. These additional structural nucleic acid sequences may generally be any sequences suitable for use in a recombinant vector. Such structural nucleic acid sequences include any of the structural nucleic acid sequences, and modified forms thereof, described above. Additional structural nucleic acid sequences may also be operably linked to any of the above described promoters. One or more structural nucleic acid sequences may each be operably linked to separate promoters. Alternatively, the structural nucleic acid sequences may be operably linked to a single promoter (i.e. a single operon).

Additional structural nucleic acid sequences preferably encode seed storage proteins, herbicide resistance proteins, disease resistance proteins, fatty acid biosynthetic enzymes, tocopherol biosynthetic enzymes, amino acid biosynthetic enzymes, or insecticidal proteins. Preferred structural nucleic acid sequences include, but are not limited to, gamma methyltransferase, phytyl prenyltransferase, β-ketoacyl-CoA synthase, fatty acyl-CoA reductase, fatty acyl CoA:fatty alcohol transacylase, anthranilate synthase, threonine deaminase, acetohydroxy acid synthase, aspartate kinase, dihydroxy acid synthase, aspartate kinase, dihydropicolinate synthase, thioesterase, 7S (vicilin-type) seed storage proteins (e.g. soybean β-conglycinin, P. vulgaris phaseolin, maize globulin), 11S (legumin-type) seed storage proteins (e.g. soybean glycinin), maize zeins, seed albumins, and seed lectins.

Alternatively, a second structural nucleic acid sequence may be designed to down-regulate a specific nucleic acid sequence. This is typically accomplished by operably linking the second structural amino acid, in an antisense orientation, with a promoter. One of ordinary skill in the art is familiar with such antisense technology. Any nucleic acid sequence may be negatively regulated in this manner. Preferable target nucleic acid sequences contain a low content of essential amino acids, yet are expressed at relatively high levels in particular tissues. For example, β-conglycinin and glycinin are expressed abundantly in seeds, but are nutritionally deficient with respect to essential amino acids. This antisense approach may also be used to effectively remove other undesirable proteins, such as antifeedants (e.g., lectins), albumin, and allergens, from plant-derived foodstuffs.

Selectable Markers

The recombinant vector may further comprise a selectable marker. A nucleic acid sequence serving as the selectable marker functions to produce a phenotype in cells which facilitates their identification relative to cells not containing the marker.

Examples of selectable markers include, but are not limited to: a neo gene (Potrykus et al., 1985), which codes for kanamycin resistance and can be selected for using kanamycin, G418, etc.; a bar gene which codes for bialaphos resistance; a mutant EPSP synthase gene (Hinchee et al., 1988) which encodes glyphosate resistance; a nitrilase gene which confers resistance to bromoxynil (Stalker et al., 1988); a mutant acetolactate synthase gene (ALS) which confers imidazolinone or sulphonylurea resistance (European Application 0 154 204); green fluorescent protein (GFP); and a methotrexate resistant DHFR gene (Thillet et al., 1988).

Other exemplary selectable markers include: a β-glucuronidase or uidA gene (GUS), which encodes an enzyme for which various chromogenic substrates are known (Jefferson (I), 1987; Jefferson (II) et al., 1987); an R-locus gene, which encodes a product that regulates the production of anthocyanin pigments (red color) in plant tissues (Dellaporta et al., 1988); a β-lactamase gene (Sutcliffe et al., 1978), which encodes an enzyme for which various chromogenic substrates are known (e.g., PADAC, a chromogenic cephalosporin); a luciferase gene (Ow et al., 1986); a xylE gene (Zukowsky et al., 1983) which encodes a catechol dioxygenase than can convert chromogenic catechols; an α-amylase gene (Ikatu et al., 1990); a tyrosinase gene (Katz et al., 1983), which encodes an enzyme capable of oxidizing tyrosine to DOPA and dopaquinone (which in turn condenses to melanin); and an α-galactosidase, which will alter the color of a chromogenic α-galactose substrate.

Included within the phrase "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

Other Elements in the Recombinant Vector

Various cis-acting untranslated 5' and 3' regulatory sequences may be included in the recombinant nucleic acid vector. Any such regulatory sequences may be provided in a recombinant vector with other regulatory sequences. Such combinations can be designed or modified to produce desirable regulatory features.

A 3' non-translated region typically provides a transcriptional termination signal, and a polyadenylation signal which functions in plants to cause the addition of adenylate nucleotides to the 3' end of the mRNA. These may be obtained from the 3' regions of the nopaline synthase (nos) coding sequence, the soybean 7S (β-conglycinin) storage protein coding sequence, the arcelin-5 coding sequence, the albumin coding sequence, and the pea ssRUBISCO E9 coding sequence. Particularly preferred 3' nucleic acid sequences include Arcelin-5 3', nos 3', E9 3', adr12 3', β-conglycinin 3', glycinin 3', USP 3',and albumin 3'.

Typically, nucleic acid sequences located a few hundred base pairs downstream of the polyadenylation site serve to terminate transcription. These regions are required for efficient polyadenylation of transcribed mRNA.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Preferred 5' nucleic acid sequences include dSSU 5', PetHSP70 5', and GmHSP17.9 5'.

The recombinant vector may further comprise a nucleic acid sequence encoding a transit peptide. This peptide may be useful for directing a protein to the extracellular space, a chloroplast, or to some other compartment inside or outside of the cell (see, e.g., European Application EP 0 218 571).

The structural nucleic acid sequence in the recombinant vector may comprise introns. The introns may be heterologous with respect to the structural nucleic acid sequence. Preferred introns include the rice actin intron and the corn HSP70 intron.

Fusion Proteins

Any of the above described structural nucleic acid sequences, and modified forms thereof, may be linked with additional nucleic acid sequences to encode fusion proteins. The additional nucleic acid sequence preferably encodes at least 1 amino acid, peptide, or protein. Production of fusion proteins is routine in the art and many possible is routine in the art any many possible fusion combinations exist.

For instance, the fusion protein may provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids.

Alternatively, the fusion may provide regulatory, enzymatic, cell signaling, or intercellular transport functions. For example, a sequence encoding a chloroplast transit peptide may be added to direct a fusion protein to the chloroplasts within seeds. Such fusion partners preferably encode between 1 and 1000 additional amino acids, more preferably between 5 and 500 additional amino acids, and even more preferably between 10 and 250 additional amino acids.

Sequence Analysis

In the present invention, sequence similarity or identity is preferably determined using the "Best Fit" or "Gap" programs of the Sequence Analysis Software Package™ (Version 10; Genetics Computer Group, Inc., University of Wisconsin Biotechnology Center, Madison, Wis.). "Gap" utilizes the algorithm of Needleman and Wunsch (Needleman and Wunsch, 1970) to find the alignment of two sequences that maximizes the number of matches and minimizes the number of gaps. "BestFit" performs an optimal alignment of the best segment of similarity between two sequences. Optimal alignments are found by inserting gaps to maximize the number of matches using the local homology algorithm of Smith and Waterman (Smith and Waterman, 1981; Smith et al., 1983).

The Sequence Analysis Software Package described above contains a number of other useful sequence analysis tools for identifying homologues of the presently disclosed nucleotide and amino acid sequences. For example, the "BLAST" program (Altschul et al., 1990) searches for sequences similar to a query sequence (either peptide or nucleic acid) in a specified database (e.g., sequence databases maintained at the National Center for Biotechnology Information (NCBI) in Bethesda, Md, USA); "FastA" (Lipman and Pearson, 1985; see also Pearson and Lipman, 1988; Pearson, 1990) performs a Pearson and Lipman search for similarity between a query sequence and a group of sequences of the same type (nucleic acid or protein); "TfastA" performs a Pearson and Lipman search for similarity between a protein query sequence and any group of nucleotide sequences (it translates the nucleotide sequences in all six reading frames before performing the comparison); "FastX" performs a Pearson and Lipman search for similarity between a nucleotide query sequence and a group of protein sequences, taking frameshifts into account. "TfastX" performs a Pearson and Lipman search for similarity between a protein query sequence and any group of nucleotide sequences, taking frameshifts into account (it translates both strands of the nucleic acid sequence before performing the comparison).

Probes and Primers

Short nucleic acid sequences having the ability to specifically hybridize to complementary nucleic acid sequences may be produced and utilized in the present invention. These short nucleic acid molecules may be used as probes to identify the presence of a complementary nucleic acid sequence in a given sample. Thus, by constructing a nucleic acid probe which is complementary to a small portion of a particular nucleic acid sequence, the presence of that nucleic acid sequence may be detected and assessed.

Any of the nucleic acid sequences disclosed herein may be used as a primer or probe. Use of these probes or primers may greatly facilitate the identification of transgenic plants which contain the presently disclosed promoters and structural nucleic acid sequences. Probes may also be used to screen cDNA or genomic libraries for additional nucleic acid sequences related to or sharing homology with the presently disclosed promoters and structural nucleic acid sequences.

Alternatively, short nucleic acid sequences may be used as oligonucleotide primers to amplify or mutate a complementary nucleic acid sequence using PCR technology. These primers may also facilitate the amplification of related complementary nucleic acid sequences (e.g., related nucleic acid sequences from other species).

Short nucleic acid sequences may be used as probes and specifically as PCR probes. A PCR probe is a nucleic acid molecule capable of initiating a polymerase activity while in a double-stranded structure with another nucleic acid. Various methods for determining the structure of PCR probes and PCR techniques exist in the art. Computer generated searches using programs such as Primer3 (www.genome.wi.mit.edu/cgi-bin/primer/primer3.cgi), STSPipeline (www.genome.wi.mit.edu/cgi-bin/www.STS_Pipeline), or GeneUp (Pesole et al., 1998), for example, can be used to identify potential PCR primers.

A primer or probe is generally complementary to a portion of a nucleic acid sequence that is to be identified, amplified, or mutated, and should be of sufficient length to form a stable and sequence-specific duplex molecule with its complement. A primer or probe preferably is about 10 to about 200 nucleotides long, more preferably is about 10 to about 100 nucleotides long, even more preferably is about 10 to about 50 nucleotides long, and most preferably is about 14 to about 30 nucleotides long.

The primer or probe may, for example, be prepared by direct chemical synthesis, by PCR (U.S. Pat. Nos. 4,683,195 and 4,683,202), or by excising the nucleic acid specific fragment from a larger nucleic acid molecule.

Transgenic Plants and Transformed Plant Host Cells

The present invention is also directed to transgenic plants and transformed host cells which comprise, in a 5' to 3' orientation, any of the nucleic acids disclosed herein. Other nucleic acid sequences may also be introduced into the plant or host cell along with the nucleic acid sequence of the present invention. These other sequences may include 3' transcriptional terminators, 3' polyadenylation signals, other untranslated nucleic acid sequences, transit or targeting sequences, selectable markers, enhancers, and operators. Preferred nucleic acid sequences of the present invention, including recombinant vectors, structural nucleic acid sequences, promoters, and other regulatory elements, are described above.

Means for preparing such recombinant vectors are well known in the art. For example, methods for making recombinant vectors particularly suited to plant transformation are described in U.S. Pat. Nos. 4,971,908; 4,940,835; 4,769,061; and 4,757,011. These vectors have also been reviewed (Rodriguez et al., 1988; Glick et al., 1993) and are described above.

Typical vectors useful for expression of nucleic acids in cells and higher plants are well known in the art and include vectors derived from the tumor-inducing (Ti) plasmid of *Agrobacterium tumefaciens* (Rogers et al., 1987). Other recombinant vectors useful for plant transformation, have also been described (Fromm et al., 1985). Elements of such recombinant vectors are discussed above.

A transformed plant cell or plant may generally be any cell or plant which is compatible with the present invention.

The plant or plant cell preferably is an alfalfa, apple, banana, barley, bean, broccoli, cabbage, carrot, castorbean, celery, citrus, clover, coconut, coffee, corn, cotton, cucumber, Douglas fir, Eucalyptus, garlic, grape, linseed, Loblolly pine, melon, oat, olive, onion, palm, parsnip, pea, peanut, pepper, poplar, potato, radish, Radiata pine, rapeseed, rice, rye, sorghum, *Lupinus angustifolius,* Southern pine, soybean, spinach, strawberry, sugarbeet, sugarcane, sunflower, Sweetgum, tea, tobacco, tomato, turf, or wheat plant or cell. In a more preferred embodiment, the plant or plant cell is soybean, corn, or wheat. In an even more preferred embodiment, the plant or plant cell is soybean.

The soybean cell or plant is preferably an elite soybean cell line. An "elite line" is any line that has resulted from breeding and selection for superior agronomic performance. Examples of elite lines are lines that are commercially available to farmers or soybean breeders such as HARTZ™ variety H4994, HARTZ™ variety H5218, HARTZ™ variety H5350, HARTZ™ variety H5545, HARTZ™ variety H5050, HARTZ™ variety H5454, HARTZ™ variety H5233, HARTZ™ variety H5488, HARTZ™ variety HLA572, HARTZ™ variety H6200, HARTZ™ variety H6104, HARTZ™ variety H6255, HARTZ™ variety H6586, HARTZ™ variety H6191, HARTZ™ variety H7440, HARTZ™ variety H4452 Roundup Ready™, HARTZ™ variety H4994 Roundup Ready™, HARTZ™ variety H4988 Roundup Ready™, HARTZ™ variety H5000 Roundup Ready™, HARTZ™ variety H5147 Roundup Ready™, HARTZ™ variety H5247 Roundup Ready™, HARTZ™ variety H5350 Roundup Ready™, HARTZ™ variety H5545 Roundup Ready™, HARTZ™ variety H5855 Roundup Ready™, HARTZ™ variety H5088 Roundup Ready™, HARTZ™ variety H5164 Roundup Ready™, HARTZ™ variety H5361 Roundup Ready™, HARTZ™ variety H5566 Roundup Ready™, HARTZ™ variety H5181 Roundup Ready™, HARTZ™ variety H5889 Roundup Ready™, HARTZ™ variety H5999 Roundup Ready™, HARTZ™ variety H6013 Roundup Ready™, HARTZ™ variety H6255 Roundup Ready™, HARTZ™ variety H6454 Roundup Ready™, HARTZ™ variety H6686 Roundup Ready™, HARTZ™ variety H7152 Roundup Ready™, HARTZ™ variety H7550 Roundup Ready™, HARTZ™ variety H8001 Roundup Ready™ (HARTZ SEED, Stuttgart, AR); A0868, AG0901, A1553, A1900, AG1901, A1923, A2069, AG2101, AG2201, A2247, AG2301, A2304, A2396, AG2401, AG2501, A2506, A2553, AG2701, AG2702, A2704, A2833, A2869, AG2901, AG2902, AG3001, AG3002, A3204, A3237, A3244, AG3301, AG3302, A3404, A3469, AG3502, A3559, AG3601, AG3701, AG3704, AG3750, A3834, AG3901, A3904, A4045 AG4301, A4341, AG4401, AG4501, AG4601, AG4602, A4604, AG4702, AG4901, A4922, AG5401, A5547, AG5602, A5704, AG5801, AG5901, A5944, A5959, AG6101, QR4459, and QP4544 (Asgrow Seeds, Des Moines, IA); DeKalb variety CX445 (DeKalb, IL).

The present invention is also directed to a method of producing transformed plants which comprise, in a 5' to 3' orientation, a nucleic acid sequence of the present invention. Other sequences may also be introduced into plants along with the promoter and structural nucleic acid sequence. These other sequences may include, without limitation, 3' transcriptional terminators, 3' polyadenylation signals, other untranslated sequences, transit or targeting sequences, selectable markers, enhancers, and operators. Preferred recombinant vectors, structural nucleic acid sequences, promoters, and other regulatory elements are described herein.

The method generally comprises the steps of selecting a suitable plant, transforming the plant with a recombinant vector, and obtaining the transformed host cell.

There are many methods for introducing nucleic acid into plants. Suitable methods include bacterial infection (e.g., *Agrobacterium*), binary bacterial artificial chromosome vectors, direct delivery of nucleic acids (e.g., via PEG-mediated transformation, dessiccation/inhibition-mediated nucleic acid uptake, electroporation, agitation with silicon carbide fibers, and acceleration of nucleic acid coated particles, etc. (reviewed in Potrykus et al., 1991).

Technology for introduction of nucleic acids into cells is well known to those of skill in the art. Methods can generally be classified into four categories: (1) chemical methods (Graham and van der Eb, 1973; Zatloukal et al., 1992); (2) physical methods such as microinjection (Capecchi, 1980), electroporation (Wong and Neumann, 1982; Fromm et al., 1985; U.S. Pat. No. 5,384,253), and particle acceleration (Johnston and Tang, 1994; Fynan et al., 1993); (3) viral vectors (Clapp, 1993; Lu et al., 1993; Eglitis and Anderson, 1988); and (4) receptor-mediated mechanisms (Curiel et al., 1992; Wagner et al., 1992). Alternatively, nucleic acids can be directly introduced into pollen by directly injecting a plant's reproductive organs (Zhou et al., 1983; Hess, 1987; Lou et al., 1988; Pena et al., 1987). Nucleic acids may also be injected into immature embryos (Neuhaus et al., 1987).

A recombinant vector used to transform the host cell typically comprises, in a 5' to 3' orientation: a promoter to direct the transcription of a structural nucleic acid sequence, a structural nucleic acid sequence, a 3' transcriptional terminator, and a 3' polyadenylation signal. The recombinant vector may further comprise untranslated nucleic acid sequences, transit and targeting nucleic acid sequences, selectable markers, enhancers, or operators.

Suitable recombinant vectors, structural nucleic acid sequences, promoters, and other regulatory elements are described above.

Regeneration, development, and cultivation of plants from transformed plant protoplast or explants is taught in the art (Weissbach and Weissbach, 1988; Horsch et al., 1985). In this method, transformants are generally cultured in the presence of a selective media which selects for the successfully transformed cells and induces the regeneration of plant shoots (Fraley et al., 1983). These shoots are typically obtained within 2 to 4 months.

Shoots are then transferred to an appropriate root-inducing medium containing the selective agent and an antibiotic to prevent bacterial growth. Many of the shoots will develop roots. These are then transplanted to soil or other media to allow the continued development of roots. A method will generally vary depending on the particular plant strain employed.

Preferably, the regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the nucleic acid sequence encoding the enhanced gene expression to its progeny. The transgenic plant is preferably homozygous for the nucleic acid encoding the enhanced gene expression and transmits that sequence to all of its offspring upon as a result of sexual reproduction. Progeny may be grown from seeds produced by the transgenic plant. These additional plants may then be self-pollinated to generate a true breeding line of plants.

The progeny from these plants are evaluated, among other things, for gene expression. The gene expression may be detected by several common methods such as western blotting, nothern blotting, immunoprecipitation, and ELISA.

Seed Containers

Seeds of a plant or plants of the present invention may be placed in a container. As used herein, a container is any object capable of holding such seeds. A container preferably contains greater than 1,000, 5,000, or 25,000 seeds where at least 10%, 25%, 50%, 75%, or 100% of the seeds are derived from a plant of the present invention.

Feed, Meal, Protein and Oil Preparations

Any of the plants or parts thereof of the present invention may be processed to produce a feed, meal, protein or oil preparation. A particularly preferred plant part for this purpose is a seed. In a preferred embodiment the feed, meal, protein or oil preparation is designed for ruminant animals. Methods to produce feed, meal, protein and oil preparations are known in the art. See, for example, U.S. Pat. Nos. 4,957,748; 5,100,679; 5,219,596; 5,936,069; 6,005,076; 6,146,669; and 6,156,227. In a preferred embodiment, the protein preparation is a high protein preparation. Such a high protein preparation preferably has a protein content of greater than 5% w/v, more preferably 10% w/v, and even more preferably 15% w/v. In a preferred oil preparation, the oil preparation is a high oil preparation with an oil content derived from a plant or part thereof of the present invention of greater than 5% w/v, more preferably 10% w/v, and even more preferably 15% w/v. In a preferred embodiment the oil preparation is a liquid and of a volume greater than 1, 5, 10, or 50 liters. In another embodiment, the oil preparation may be blended and can constitute greater than 10%, 25%, 35%, 50%, or 75% of the blend by volume.

Other Organisms

Any of the above described nucleic acid sequences may be introduced into any cell or organism such as a mammalian cell, mammal, fish cell, fish, bird cell, bird, algae cell, algae, fungal cell, fungi, or bacterial cell. Preferred hosts and transformants include: fungal cells such as *Aspergillus,* yeasts, mammals (particularly bovine and porcine), insects, bacteria and algae. Particularly preferred bacteria cells are *Agrobacterium* and *E. coli.*

In another particularly preferred embodiment, the cell is selected from the group consisting of a bacteria cell, a mammalian cell, an insect cell, and a fungal cell.

Methods to transform such cells or organisms are known in the art (EP 0 238 023; Yelton et al., 1984; Malardier et al., 1989; Becker and Guarente; Ito et al., 1983; Hinnen et al., 1978; and Bennett and LaSure, 1991). Methods to produce proteins of the present invention from such organisms are also known (Kudla et al., 1990; Jarai and Buxton, 1994; Verdier, 1990; MacKenzie et al., 1993; Hartl et al., 1994; Bergeron et al., 1994; Demolder et al., 1994; Craig, 1993; Gething and Sambrook, 1992; Puig and Gilbert, 1994; Wang and Tsou, 1993; Robinson et al., 1994; Enderlin and Ogrydziak, 1994; Fuller et al., 1989; Julius et al., 1984; and Julius et al., 1983).

Exemplary Uses of the Invention

Uses of the present invention include nutritional supplementation for animals, including humans. The supplementation forms for animals include feed rations, meal, and protein isolates from grain. The supplementation forms for humans include soy protein isolates and infant formula.

In a preferred embodiment, proteins, seeds, and plants of the present invention are used in human food. As used herein, "human food" refers to any food fit for human consumption. In a preferred embodiment, human food is any food that is derived from agricultural sources, whether directly in the form of plant products or indirectly in the form of animal products that are derived from animals that fed on plants from agricultural sources. In a further preferred embodiment, human food is any food that is derived from plants or seeds of the present invention, whether directly in the form of plant products or indirectly in the form of animal products that are derived from animals that fed on plants from agricultural sources. In another embodiment, human food is any food that is derived from soybean plants or seeds of the present invention, whether directly in the form of soybean plant products of the present invention or indirectly in the form of animal products that are derived from animals that fed on soybean plants of the present invention.

The following examples are illustrative only. It is not intended that the present invention be limited to the illustrative embodiments.

EXAMPLES

The following examples are exemplary only, and do not limit the scope of the invention.

Example 1

Preparation of total RNA from immature-soybean seeds.

Approximately 180 mg of immature soybean seeds (Asgrow A3244) are ground into a powder and added to a 15 ml centrifuge tube. 2.5 ml of TRIZOL™ (GIBCO Life Technologies, Inc., Rockville, MD) is added to the tube and the sample is homogenized using a Polytron™ (Model PT 1200, Brinkmann Instruments, Inc., Westbury, NY) mixer for 20 to 30 seconds. The sample is incubated at room temperature for 5 minutes, and 0.5 ml of chloroform is added to the homogenate. The tube is shaken vigorously and allowed to stand for 2 to 3 minutes at room temperature. The samples are centrifuged at 12,000X g for 15 minutes at 4° C. The aqueous phase is transferred to a fresh 15 ml tube, 1.25 ml of isopropyl alcohol is added, and the contents are mixed and incubated at room temperature for 10 minutes. The tube is centrifuged at 12,000X g for 10 minutes at 4° C., and the supernatant is discarded. The pellet is resuspended in 2.5 ml of 75% ethanol and centrifuged at 7,500X g for 5 minutes at 4° C. The supernatant is discarded and the pellet is dissolved in 400 μl of $H_2O$.

Example 2

Preparing a glycinin $A_{1a}B_{1b}$ cDNA clone from immature soybean seed total RNA using the Titan™ One Tube RT-PCR system (Boehringer Mannheim, Indianapolis, IN).

The following oligonucleotide primers are obtained from GibcoBRL:

Primer 1: CAC TCA TCA GTC ATC ACC [SEQ ID NO: 3].

Primer 2: GGT TGC TAG CAC TAT TGC [SEQ ID NO: 4].

RT-PCR reactions are assembled in 0.2 ml PCR tubes according to the protocol supplied with the Titan™ One Tube RT-PCR System. The reaction contains:

1 μl 10 mM dNTP mix (10 mM each dATP, dCTP, dGTP, dTTP)

2 μl 10 mM Primer 1

2 μl 10 mM Primer 2

1 μl soybean total RNA (0.7 μg/μl)

2.5 μl 100 mM DTT

1 μl RNasin RNase inhibitor (Promega, 5 units/μl)

29.5 μl $H_2O$

10 μl 5X RT-PCR Buffer

1 μl Enzyme Mix

An RT-PCR is performed on a PTC-200 Peltier Thermocycler using the following program sequence: 1) 50° C. for 30 minutes; 2) 94° C. for 2 minutes; 3) 94° C. for 30 seconds; 4) 45° C. for 30 seconds; 5) 68° C. for 90 seconds; 6) Go to step (3) and repeat for 9 additional cycles; 7) 94° C. for 30 seconds; 8) 45° C. for 30 seconds; 9) 68° C. for 90 seconds; 10) Go to step 7, repeat for 9 additional cycles plus 5 seconds each cycle; 11) 68° C. for 7 minutes; 12) Cool to 4° C. and end program.

The PCR reaction products are separated on an agarose gel. PCR fragments are excised from gel and purified using standard protocols and ligated into the pCR2.1-TOPO™ vector using the TA™ cloning kit (Invitrogen, Carlsbad, CA). Ligation is performed according to the manufacturer's protocol.

The ligated vectors containing the PCR products are transformed into One Shot™ (Invitrogen, Carlsbad, CA) competent cells (*E. coli* INVαF'strain) according to the manufacturer's protocol.

Plasmid DNA is isolated from transformed colonies using a QIAprep™ (Qiagen Inc., Velencia, CA) miniprep kit, according to the manufacturer's protocols. A sample from each of the DNA minipreps is digested separately with EcoRI and BglII, and the resulting DNA fragments are separated on an agarose gel. The BglII digestion yields 4.0 and 1.38 kb fragments. The EcoRI digestion yields 3.9, 0.87, and 0.70 kb fragments. The DNA sequences of the inserts are determined, and confirmed to represent full-length glycinin $A_{1a}B_{1b}$ cDNAs based on comparisons to previously published sequences. Plasmid pMON65953 (FIG. 1) is used as a template in subsequent subcloning and mutagenesis experiments (described below) the derived amino acid sequence from the glycinin $A_{1a}B_{1b}$ cDNA in this plasmid [SEQ ID NO: 2] exhibits a 100% match to that of a glycinin $A_{1a}B_{1b}$ cDNA published by Nielsen et. al. (Plant Cell, vol. 11, pp. 313–328, 1989).

Example 3

Expression and self-assembly of epitope-tagged modified glycinin $A_{1a}B_{1b}$ in *E. coli.*

In order to distinguish modified forms of glycinin $A_{1a}B_{1b}$ from the endogenous form that accumulates in non-transformed soybeans, forms of glycinin $A_{1a}B_{1b}$ are created that contain a "FLAG" epitope coding sequence attached to the coding sequence representing either the amino-terminus, or the carboxy-terminus, of the mature form of the protein (i.e., the form lacking the signal peptide). The FLAG epitope consists of the sequence Asp-Tyr-Lys-Asp-Asp-Asp-Asp-Lys [SEQ ID NO: 5], and is encoded by SEQ ID NO: 6 (5' GAC TAC AAG GAC GAC GAT GAC AAG 3').

The FLAG coding sequence, plus an additional methionine codon to serve as a translation start codon, is added onto the amino-terminus of the mature glycinin $A_{1a}B_{1b}$ protein coding sequence by standard PCR technology using pMON 65953 as a template, and according to the manufacturer's directions (Boehringer Mannheim, Indianapolis, Ind., Expand High Fidelity PCR System). The following PCR primers were used:

Primer Gly-P10: (5') ATA GCC ATG GAC TAC AAG GAC GAC GAT GAC AAG TTC AGT TCC AGA GAG CAG CCT (3') [SEQ ID NO: 7]; and Primer M13-Reverse: (5') CAG GAA ACA GCT ATG AC (3') [SEQ ID NO: 8]

Figure 2:
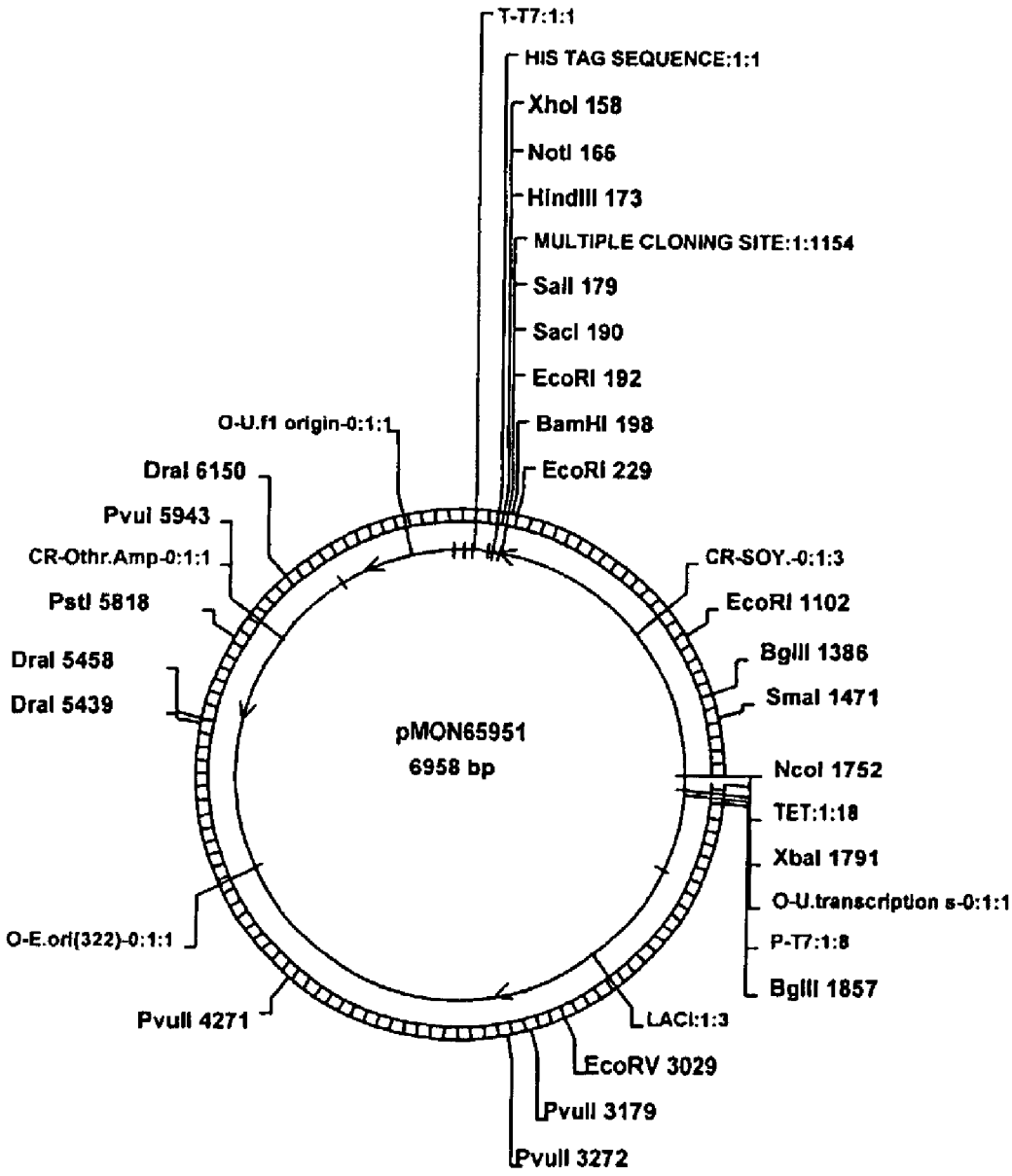
FIG. 2 is a plasmid map of pMON65951.

The resulting 1.6 kb PCR product is digested with NcoI + BamHI and cloned into the NcoI and BamHI sites of *E. coli* expression vector, pET21d(+) (Novagen, Madison, WI), to create pMON65951, which is shown in FIG. 2.

The amino-terminal epitope (FLAG)-tagged form of the modified glycinin $A_{1a}B_{1b}$ encoded by pMON65951 has the amino acid sequence of SEQ ID NO: 9.

The nucleotide sequence in pMON65951 encoding the amino-terminal epitope (FLAG)-tagged form of the modified glycinin $A_{1a}B_{1b}$ has the sequence of SEQ ID NO: 10.

Figure 3:
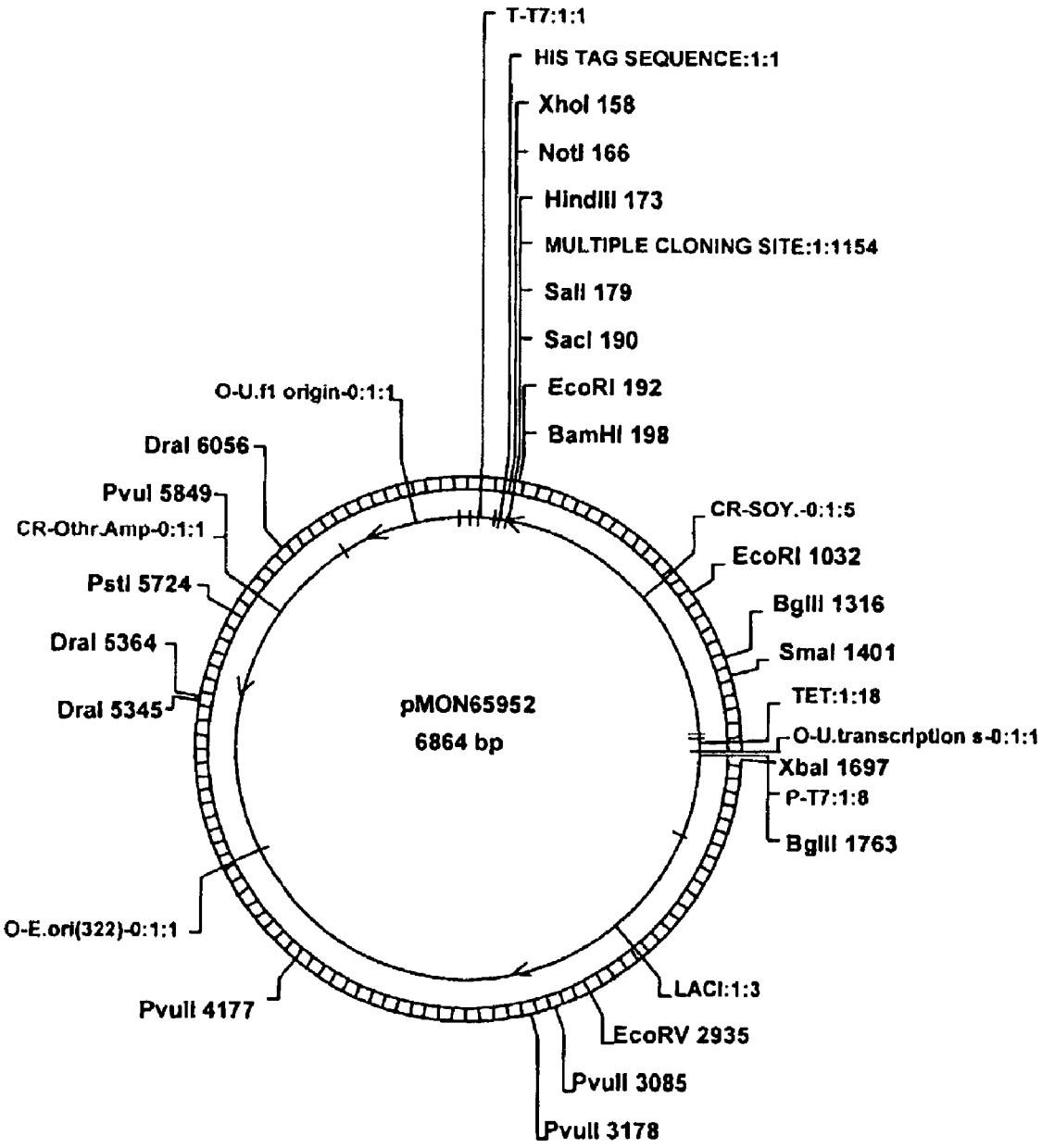
FIG. 3 is a plasmid map of pMON65952.

A second plasmid, pMON65952, shown in FIG. 3, is created that contains the coding sequence for the mature form of glycinin $A_{1a}B_{1b}$ with the FLAG epitope at the carboxy-terminus in pET21d(+). The FLAG coding sequence is added onto the carboxy-terminus of the mature glycinin $A_{1a}B_{1b}$ protein coding sequence by standard PCR technology using pMON65953 as a template, and according to the manufacturer's directions (Boehringer Mannheim, Indianapolis, IN, Expand high Fidelity PCR System). The following PCR primers were used:

Primer Gly-P9: (5') TTC AGT TCC AGA GAG CAG C (3') [SEQ ID NO: 11]; and

Primer Gly-P11: (5') ACG CGG ATC CCT ACT TGT CAT CGT CGT CCT TGT AGT CAG CCA CAG CTC TCT TCT GAG AC (3') [SEQ ID NO: 12]

After removing any single base-pair overhangs from the resulting 1.5 kb PCR product by incubation with Klenow fragment, the PCR product is digested with BamHI. The backbone vector pET21d(+) is prepared by digesting with NcoI, filling in the NcoI overhangs using Klenow fragment, and then digesting with BamHI. To create pMON65952, the PCR product, with one blunt-end and one BamHI overhang, is then ligated into the linearized pET21d(+) vector, which also contains one blunt-end and one BamHI overhang, and transformed into compentent *E. coli* DH5α cells according to standard methods.

The carboxy-terminal epitope (FLAG)-tagged form of the modified glycinin $A_{1a}B_{1b}$ encoded by pMON65952 has the amino acid sequence of SEQ ID NO: 13.

The nucleotide sequence in pMON65952 encoding the epitope (FLAG)-tagged form of the modified glycinin $A_{1a}B_{1b}$ has the sequence of SEQ ID NO: 14.

Figure 4:
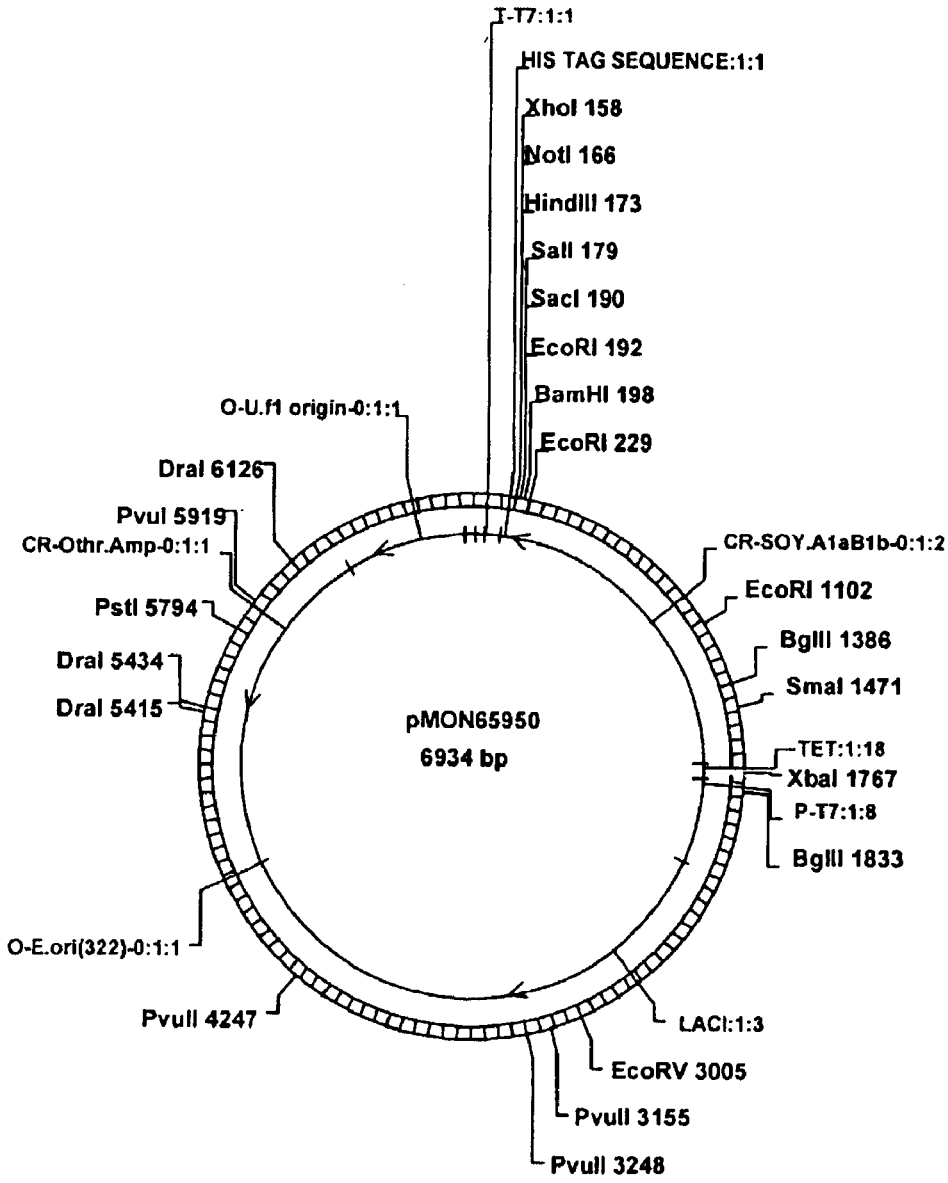
FIG. 4 is a plasmid map of pMON65950.

A third plasmid, pMON65950, shown in FIG. 4, is created that contains the coding sequence for the mature form (without the FLAG epitope) in pET21d(+).

The mature form (plus additional methionine encoded by start codon) of the modified glycinin $A_{1a}B_{1b}$ encoded by pMON65950 has the amino acid sequence of SEQ ID NO: 15.

The nucleotide sequence in pMON65950 encoding the mature form of the modified glycinin $A_{1a}B_{1b}$ has the sequence of SEQ ID NO: 16.

To characterize the expression of the wild-type and epitope-tagged (mature) glycinin $A_{1a}B_{1b}$ protein in *E. coli,* plasmids pMON65950, pMON65951, and pMON65952 are transformed into *E. coli* Origami™ (DE3) competent cells according to manufacturer's instructions (Novagen). A single colony is used to inoculate 2 ml LB medium. The culture is grown at 37° C. until a cell density corresponding to $A_{600}$ =0.6 is achieved. An amount corresponding to a final concentration of 1 mM isopropyl-1-thio-β-D-galactopyranoside (IPTG) is added to induce protein expression and the culture is incubated at temperatures ranging from 20° to 37° C. at 225 rpm for time periods up to 20 hours. Cells are harvested by centrifugation at 5,000 rpm for 15 min at 4° C. The cell pellet is re-suspended in protein extraction buffer consisting of 20 mM Tris-HCl, pH 7.4, 0.4 M NaCl, 0.1% TritonX-100, 40 μl/ml Protease Inhibitor Cocktail, (stock: 1 tablet/2 ml, Boehringer Mannheim, Indianapolis, IN). The cells are then disrupted by sonication (Branson Sonifier 450, Branson Precision Processing, Danbury, Conn. while maintaining at cold temperature with ice. Soluble proteins are separated from the insoluble fraction by centrifugation at 13,000 rpm for 5 minutes. Results from Coomassie staining and a Western blotting with Anti-FLAG antibody show that the solubility and expression level of the native and the (FLAG)-tagged forms are similar.

To determine if the recombinant forms of glycinin $A_{1a}B_{1b}$ expressed in *E. coli* from pMON69950, pMON65951, and pMON65952 could self-assemble to form trimers, aliquots of the soluble protein fraction from *E. coli* lysates are layered onto 12 ml of a 5–25% sucrose density gradient, and centrifuged at 36,000 rpm for 17.5 hours at 20° C. (Sorvall TH-641 rotor; Sorvall Ultra Pro 80 ultracentrifuge). Following centrifugation, the gradient is divided into fractions using a Labconco Autodensi-Flow instrument (Labconco, Kansas City, Mo.), and each fraction is analyzed by SDS-polyacrylamide gel electrophoresis followed either by Coomassie staining or by western blot analysis using Anti-FLAG M2 antibody (Stratagene Corporation, LaJolla, Calif.), to determine which fractions contained glycinin $A_{1a}B_{1b}$. 7S and 11S soy protein fractions, as well as ovalbumin (45 kD) and aldolase (158 kD), are run as size markers on separate gradients. Comparisons of the sedimentation properties of the wild-type and epitope-tagged glycinin $A_{1a}B_{1b}$ proteins with protein standards indicates that all three recombinant proteins had self-assembled to form trimers.

Example 4

Computational Strategy

The soy glycinin crystal structure ProA1aB1b (PDB Id 1FXZ) (M. Adachi, et al., *J. Mol. Biol.,* 305:291–305 (2001)) is energy minimized using the default MMFF force field [SOFTWARE]. The optimization method used is conjugate gradient and the convergence criterion is set to $\Delta E > 0.05$ kcal/mol between successive iterations. The dielectric constant during minimization is set to 4.0, representing a typical non-polar (organic) dielectric environment. (All of these parameters are standard for protein modeling.) The Root-Mean-Square Distance (RMSD) of the backbone between the initial crystal structure and the minimized structure is 0.81 Å. This is within acceptable limits considering the size of the homo-trimer (1147 residues), thus providing support for the computational approach employed. Most structural features are wholly aligned except for some loop structures close to the surface. Further calculations and AA alterations are based on this energy-minimized crystal structure.

During simulations residues are altered "three-at-a-time" as a reasonable compromise between computational efficiency and theoretical accuracy. Thus, different LEU, PHE and ALA "triplets" are mutated to ILE. For each AA mutation, the side-chain is altered accordingly and a local energy minimization performed. (Note that mutation of a single residue in the monomer corresponds to mutation of three residues in the homo-trimer).

Following local energy minimization, the entire modified protein trimer is subjected to full energy minimization. By allowing the altered protein to relax in steps, this procedure minimizes the risk of introducing unrealistic changes in the protein structure resulting from local modifications.

After each set of AAs is altered to the appropriate number of ILEs, and the resulting structure subjected to energy minimization, the backbone RMSD between the altered structure and the original minimized crystal structure is calculated. An alteration is considered acceptable if RMSD is less than 1.0 Å. Some AA alterations are designated as "high risk" if the altered residues exist within 5 Å proximity of one of the monomer—monomer interfaces. Similarly, alterations are designated as "medium risk" if the altered residues exist within 5 Å–10 Å proximity of one of the monomer—monomer interfaces. It is reasonable to assume that significant alterations within these regions could disrupt the formation and/or stability of the trimeric structure. This, in turn, might lead to loss of proper formation of the trimeric protein within the biological system.

Fortunately, although every LEU, PHE and ALA in the protein is altered to ILE, the RMSD remains nearly within the acceptable limit despite the fact that some of the altered residues exit in the "high risk" region or/and "medium risk" region.

Alterations of leucine to isoleucine, phenylalanine to isoleucine and alanine to isoleucine were carried out in consecutive order (Tables X-X). The percentage of ILE finally reached is 21.5% (Table X). Risk assessments (below the tables) are based upon the spatial locations of the AAs in question with an increased risk associated with close proximity to monomer—monomer contact faces.

TABLE X

Results of leucine to isoleucine alterations.

| LEU # | Cumulative number of alterations in monomer | Cumulative % ILE | Cumulative RMSD | ΔRMSD |
|---|---|---|---|---|
| Initial structure | 0 | 5.5 | — | — |
| 20,152,366 | 3 | 6.1 | 0.038 | 0.038 |
| 122,333,345 | 6 | 6.8 | 0.14 | 0.110 |
| 17,32,371 | 9 | 7.4 | 0.16 | 0.049 |
| 50,328,387 | 12 | 8.0 | 0.18 | 0.043 |
| 55,302,338 | 15 | 8.3 | 0.20 | 0.052 |
| 60,174,336,393,464 | 20 | 9.7 | 0.25 | 0.100 |
| 165,202,207,210,433* | 25 | 10.8 | 0.27 | 0.056 |
| 243,426,432,436** | 29 | 11.6 | 0.32 | 0.084 |
| 156,224,357,447** | 33 | 12.4 | 0.36 | 0.095 |

*Moderate risk alterations
**High risk alterations

TABLE X

Results of phenylalanine to isoleucine alterations.

| PHE # | Cumulative number of alterations in monomer | Cumulative % ILE | Cumulative RMSD | ΔRMSD |
|---|---|---|---|---|
| | 33 (LEU) | 12.4 | 0.36 | |
| 117,342,415 | 36 | 13.0 | 0.42 | 0.11 |
| 43,81,173 | 39 | 13.6 | 0.48 | 0.14 |
| 330,383,410 | 42 | 14.3 | 0.54 | 0.15 |
| 351,399,463* | 45 | 14.9 | 0.56 | 0.059 |
| 214,445,461** | 48 | 15.5 | 0.58 | 0.084 |
| 163,205,209** | 51 | 16.2 | 0.61 | 0.11 |

*Moderate risk alterations
**High risk alterations

TABLE X

Results of alanine to isoleucine alterations.

| ALA# | Cumulative number of alterations in monomer | Cumulative % ILE | Cumulative RMSD | ΔRMSD |
|---|---|---|---|---|
| | 33(LEU) + 18(PHE) | 16.2 | 0.61 | |
| 19,46,49 | 54 | 16.8 | 0.65 | 0.143 |
| 143,325,340 | 57 | 17.5 | 0.67 | 0.116 |
| 59,365,403 | 60 | 18.1 | 0.73 | 0.180 |
| 370,429 | 62 | 18.5 | 0.79 | 0.163 |
| 319,349,124,332* | 66 | 19.4 | 0.86 | 0.254 |
| 221,234,452* | 69 | 20.0 | 0.92 | 0.180 |
| 130,166,213** | 72 | 20.6 | 0.98 | 0.202 |
| 359,402,427,435** | 76 | 21.5 | 1.07 | 0.268 |

*Moderate risk alterations
**High risk alterations

Example 5

Modification of leucine residues in glycinin

This examples sets forth the modification of glycinin $A_{1a}B_{1b}$ to encode increased levels of isoleucine. The glycinin $A_{1a}B_{1b}$ subunit amino acid sequence (SEQ ID NO: 1) is modified to substitute isoleucine residues for leucine residues at the amino acid positions: L17, L20, L32, L50, L55, L60, L122, L152, L165, L202, L210, L243, L302, L328, L333, L336, L338, L345, L366, L371, L387, L393, L426, L433, or L436.

The substitutions are made using the GeneEditor™ in vitro Site-Directed Mutagenesis System (Promega Corporation, Madison, Wis.), according to the manufacturer's directions. Primers are designed to incorporate nucleotides that will change the following leucine residues in SEQ ID NO: 1 to isoleucine residues: L17, L20, L32, L50, L55, L60, L122, L152, L165, L202, L210, L243, L302, L328, L333, L336, L338, L345, L366, L371, L387, L393, L426, L433, or L436. The sequences of the primers used in the site-directed mutagenesis reactions, along with the corresponding SEQ ID NO, are listed in the table below, which displays a list of primers used in substituting isoleucine codons for leucine, phenylalanine, or tyrosine codons in the glycinin $A_{1a}B_{1b}$ coding sequence (SEQ ID NO: 2). The primer name, primer sequence (in 5' to 3' direction), and SEQ ID NO of each primer is listed. Also listed for each primer are the nucleotide substitutions that are made using that primer, and the amino acid change that results when that mutated coding sequence is translated. For example, primer GI20 is used change the CTC codon at nucleotides 58–60 of SEQ ID NO: 2, to an ATC codon, which results in an isoleucine for leucine substitution at position 20 or SEQ ID NO: 1.

| Primer Name | Primer Sequence | Amino acid substitute | Codon substitution | SEQ ID NO |
|---|---|---|---|---|
| GI20 | P-CTC AAT GCC ATC AAA CCG G | L20I | CTC58ATC | SEQ ID NO: 17 |
| GI152 | P-GAC ACC AAC AGC ATT GAG AAC CAG CTC G | L152I | TTG454ATT | SEQ ID NO: 18 |
| GI366 | P-GCA TAA TAT ACG CAA TTA ATG GAC GGG CAT TG | L366I | TTG1096ATT | SEQ ID NO: 19 |
| GI122 | P-GAG AGG GTG ATA TTA TCG CAG TGC CTA C | L122I | TTG364ATT | SEQ ID NO: 20 |
| GI333 | P-CTT CCC AGC CAT CTC GTG GC | L333I | CTC997ATC | SEQ ID NO: 21 |
| GI345 | P-GTT TGG ATC TAT CCG CAA GAA TG | L345I | CTC1033ATC | SEQ ID NO: 22 |
| GI17 | P-CCA GAT CCA AAA AAT CAA TGC CCT C | L17I | CTC49ATC | SEQ ID NO: 23 |
| GI32 | P-GAA GGA GGG ATC ATT GAG AC | L32I | CTC94ATC | SEQ ID NO: 24 |
| GI371 | P-GAA TGG ACG GGC AAT TAT ACA AGT GGT G | L371I | TTG1111ATT | SEQ ID NO: 25 |
| GI50 | P-GGT GTT GCC ATC TCT CGC TG | L50I | CTC148ATC | SEQ ID NO: 26 |
| GI328 | P-GCC ACC AGC ATT GAC TTC CC | L328I | CTT982ATT | SEQ ID NO: 27 |
| GI387 | P-GTT TGA TGG AGA GAT TCA AGA GGG ACG G | L387I | CTG1159ATT | SEQ ID NO: 28 |
| GI55 | P-CGC TGC ACC ATC AAC CGC AAC | L55I | CTC163ATC | SEQ ID NO: 29 |
| GI302 | P-CAC CAT GAG AAT TCG CCA CAA C | L302I | CTT904CTT | SEQ ID NO: 30 |
| GI338 | P-GTG GCT CAG AAT CAG TGC TG | L338I | CTC1012ATC | SEQ ID NO: 31 |
| GI60 | P-CGC AAC GCC ATT CGT AGA CC | L60I | CTT178ATT | SEQ ID NO: 32 |
| GI174 | P-GAG CAA GAG TTT ATA AAA TAT CAG CAA G | L174I | CTA520ATA | SEQ ID NO: 33 |
| GI336 | P-CTC TCG TGG ATC AGA CTC AG | L336I | CTC1006ATC | SEQ ID NO: 34 |
| GI393 | P-GAG GGA CGG GTG ATT ATC GTG CCA CAA AAC | L393I | CTG1177ATT | SEQ ID NO: 35 |
| GI464 | P-CCC TTT CAA GTT CAT TGT TCC ACC TCA GGA G | L464I | CTG1390ATT | SEQ ID NO: 36 |
| GI165 | P-GAG ATT CTA TAT TGC TGG GAA C | L165I | CTT493ATT | SEQ ID NO: 37 |
| GI202 | P-GGA GGC AGC ATA ATC AGT GGC TTC ACC C | L202I | TTG604ATC | SEQ ID NO: 38 |
| GI207 | P-GTG GCT TCA CCA TCG AAT TCT TGG AAC | L207I | CTG619ATC | SEQ ID NO: 39 |
| GI210 | P-CCC TGG AAT TCA TAG AAC ATG CAT TCA GC | L210I | TTG628ATA | SEQ ID NO: 40 |
| GI433 | P-GGG CAA ACT CAT TGA TTA ACG CAT TAC CAG AG | L433I | TTG1297ATT | SEQ ID NO: 41 |
| GI243 | P-GTG AAA GGA GGT ATT AGC GTG ATA AAA CCA CC | L243I | CTG727ATT | SEQ ID NO: 42 |
| GI426 | P-GAT CGG CAC TAT TGC AGG GGC | L426I | CTT1276ATT | SEQ ID NO: 43 |
| GI432 | P-GGG GCA AAC TCA AAT TTG AAC GCA TTA CC | L432I | TTG1294AAT | SEQ ID NO: 44 |
| GI436 | P-CAT TGT TGA ACG CAA TAC CAG AGG AAG TG | L436I | TTA1306ATA | SEQ ID NO: 45 |
| F81 | P-GTA AGG GTA TTA TTG GCA TGA TAT AC | F81I | TTT241ATT | SEQ ID NO: 46 |
| F117 | P-GAT CTA TAA CAT CAG AGA GGG TG | F117I | TTC349ATC | SEQ ID NO: 47 |
| Y134 | P-GTT GCA TGG TGG ATG ATC AAC AAT GAA GAC ACT C | Y134I | TAC400ATC | SEQ ID NO: 48 |
| F330 | P-CCA GCC TTG ACA TCC CAG CCC TC | F330I | TTC988ATC | SEQ ID NO: 49 |
| F351 | P-GAA TGC AAT GAT CGT GCC ACA CTA C | F351I | TTC1051ATC | SEQ ID NO: 50 |
| Y364 | P-GCG AAC AGC ATA ATA ATC GCA TTG AAT GGA CGG G | Y364I | TAC1090ATC | SEQ ID NO: 51 |
| F410 | P-CAG AGT GAC AAC ATC GAG TAT GTG TC | F410I | TTC1228ATC | SEQ ID NO: 52 |
| Y412 | P-CAG AGT GAC AAC TTC GAG ATT GTG TCA TTC AAG ACC | Y412I | TAT1234ATT | SEQ ID NO: 53 |
| F463 | P-CAA CCC TTT CAA GAT CCT GGT TCC AC | F463I | TTC1387ATC | SEQ ID NO: 54 |

As an example of how the glycinin $A_{1a}B_{1b}$ subunit coding sequence is modified to contain multiple isoleucine substitutions, a description of the generation of mutant ID G12-1 follows: Plasmid pMON65952 is denatured by mixing 2 μg of DNA with 2M NaOH and 2 mM EDTA and incubating at room temperature for 10 minutes. Next, the denatured template DNA is precipitated by adding 10 μl of 3 M sodium acetate (pH, 5.2) and 75 μl of 100% ethanol. After centrifugation, the DNA pellet is dissolved in 100 μl of TE buffer. The denatured DNA is immediately hybridized with the mutagenic primers as follows: 10 μl denatured pMON65952 is mixed with 1 μl top selection primer (2.9 ng/μl, from the GeneEditor™ in vitro Site-Directed Mutagenesis System), 1.25 pmol each of the following mutagenic primers: GI165, GI202, GI207, GI210, and GI433, 2 μl annealing 10 x buffer and ddH2O in a 20 μl reaction. The reaction is heated at 75° C. for 5 minutes, then cooled slowly to 37° C. on the bench-top. The mutant strand is synthesized (and nicks in the newly synthesized DNA strand are ligated) by adding 5 μl deionized water, 3 μl synthesis 10 x buffer, 1 μl T4 DNA polymerase (5–10 U) and 1 μl DNA ligase (1–3 U) in 20 μl of annealing mixture. The reaction is carried out for 90 min at 37° C. Next, 1.5 μl of the reaction is transformed into *E. coli* strain BMH71-18 mutS (Promega Corporation, Madison, Wis.), and transformed cells are grown overnight in 4 ml of LB containing 50 μl GeneEditor Antiobiotic Selection Mix (Promega Corporation, Madison, Wis.). Plasmid DNA is isolated (using Qiagen Miniprep Kit, Qiagen Inc., Valencia, Calif) from a 1.5 ml aliquot of this culture. The isolated plasmid DNA is subsequently transformed into *E. coli* strain JM109, and individual colonies are grown on LB agar plates containing 125 μg/ml ampicillin and 50 μl of GeneEditor Antibiotic Selection Mix (Promega Corporation, Madison, WI). Plasmid DNA is isolated from single colonies (Qiagen Miniprep Kit, Qiagen Inc., Valencia, Calif.) and the sequence of the glycinin $A_{1a}B_{1b}$ coding region is determined. One of these sequences is identified as mutant ID G12-1.

A list of glycinin $A_{1a}B_{1b}$ mutants containing one or more isoleucine substitutions, and the position of each substitution in each mutant, are given in the table below, which is a list of different glycinin $A_{1a}B_{1b}$ mutants and the amino acid substitutions that each contains.

| Mutant ID | AA Substitution (Codon Substitution) |
|---|---|
| g1-1 | L366I (TTG1096ATT) |
| g1-4 | L20I (CTC58ATC); L366I (TTG1096ATT) |
| g1-6 | L152I (TTG452ATT); L366I (TTG1096ATT) |
| g2-1 | L345I (CTC1033ATC) |
| g2-4 | L333I (CTC997ATC); L345I (CTC1033ATC) |
| g2-5 | L122I (TTG364ATT); L333I (CTC997ATC); L345I (CTC1033ATC) |
| g2-7 | L122I (TTG364ATT); L345I (CTC1033ATC) |
| g3-2 | L20I (CTC58ATC); L345I (CTC1033ATC) |
| g3-5 | L20I (CTC58ATC); L152I (TTG452ATT); L366I (TTG1096ATT); L122I (TTG364ATT); L333I (CTC997ATC); L345I (CTC1033ATC) |
| g3-6 | L20I (CTC58ATC); L345I (CTC1033ATC) |
| g3-7 | L20I (CTC58ATC); L122I (TTG364ATT); L345I (CTC1033ATC) |
| g3-8 | L20I (CTC58ATC); L152I (TTG452ATT); L122I (TTG364ATT); L333I (CTC997ATC); L345I (CTC1033ATC) |
| g3-9 | L20I (CTC58ATC); L366I (TTG1096ATT); L122I (TTG364ATT) |
| g4-1 | L17I (CTC49ATC); L32I (CTC64ATC); L371I (TTG1111ATT) |
| g4-2 | L17I (CTC49ATC); L32I (CTC64ATC) |
| g5-1 | L387I (CTG1159ATT) |
| g5-2 | L50I (CTC148ATC); L328I (CTT982ATT); L387I (CTG1159ATT) |
| g6-3 | L20I (CTC58ATC); L152I (TTG452ATT); L122I (TTG364ATT) |
| g6-4 | L20I (CTC58ATC); L152I (TTG452ATT); L366I (TTG1096ATT); L333I (CTC997ATC); L345I (CTC1033ATC) |
| g6-7 | L20I (CTC58ATC); L366I (TTG1096ATT); L122I (TTG364ATT); L333I (CTC997ATC); L345I (CTC1033ATC) |
| g7-1 | L122I (TTG364ATT); L333I (CTC997ATC); L345I (CTC1033ATC); L17I (CTC49ATC); L32I (CTC64ATC); L371I (TTG1111ATT) L501I (CTC148ATC); L387I (CTG1159ATT) |
| g7-2 | L32I (CTC64ATC); L371I (TTG1111ATT); L501I (CTC148ATC); L387I (CTG1159ATT) |
| g7-3 | L152I (TTG452ATT); L122I (TTG364ATT) |
| g7-6 | L17I (CTC49ATC); L32I (CTC64ATC); L387I (CTG1159ATT) |
| g7-7 | L345I (CTC1033ATC); L32I (CTC64ATC); L371I (TTG1111ATT); L387I (CTG1159ATT) |
| g7-8 | L17I (CTC49ATC); L32I (CTC64ATC) |
| g8-6 | L55I (CTC163ATC); L338I (CTC1012ATC) |
| g8-7 | L302I (CTT904CTT); L338I (CTC1012ATC) |
| g8-10 | L338I (CTC1012ATC) |
| g8-11 | L302I (CTT904CTT); L338I (CTC1012ATC); L60I (CTT158ATT) |
| g8-13 | L55I (CTC163ATC) |
| g8-14 | L50I (CTC148ATC); L302I (CTT904CTT); L338I (CTC1012ATC) |
| g8-16 | L55I (CTC163ATC); L302I (CTT904CTT); L338I (CTC1012ATC) |
| g9-1 | L174I (CTA520ATA); L393I (CTG1177ATT) |
| g9-3 | L336I (CTC1006ATC) |
| g9-5 | L336I (CTC1006ATC); L393I (CTG1177ATT); L464I (CTG1390ATT) |
| g9-6 | L393I (CTG1177ATT) |
| g9-9 | L174I (CTA520ATA) |
| g10-1 | L464I (CTG1390ATT) |
| g10-2 | L174I (CTA520ATA); L464I (CTG1390ATT) |
| g10-3 | L393I (CTG1177ATT); L464I (CTG1390ATT) |
| g10-5 | L60I (CTT158ATT); L174I (CTA520ATA); L302I (CTT904CTT); L336I (CTC1006ATC); L393I (CTG1177ATT); L464I (CTG1390ATT) |

-continued

| Mutant ID | AA Substitution (Codon Substitution) |
|---|---|
| g10-10 | L60I (CTT158ATT); L302I (CTT904CTT); L336I (CTC1006ATC); L393I (CTG1177ATT) |
| g10-15 | L60I (CTT158ATT); L302I (CTT904CTT) |
| g10-18 | L174I (CTA520ATA); L393I (CTG1177ATT); L464I (CTG1390ATT) |
| g12-1 | L202I (TTG604ATC); L210I (TTG628ATA); L433I (TTG1297ATT) |
| g12-2 | L165I (CTT493ATT); L202I (TTG604ATC); L210I (TTG628ATA); L433I (TTG1297ATT) |
| g13-1 | L202I (TTG604ATC); L243I (CTG727ATT); L426I (CTT1276ATT); L436I (TTA1306ATA) |
| g13-2 | L243I (CTG727ATT); L426I (CTT1276ATT); L436I (TTA1306ATA) |
| g15-2 | L17I (CTC49ATC); L32I (CTC64ATC); L371I (TTG1111ATT); L50I (CTC148ATC) |
| g17-1 | L20I (CTC58ATC); L152I (TTG452ATT); L366I (TTG1096ATT); L387I (CTG1159ATT) |
| g17-2 | L20I (CTC58ATC); L152I (TTG452ATT); L366I (TTG1096ATT); L50I (CTC148ATC); L328I (CTT982ATT); L387I (CTG1159ATT) |

Example 6

Further Modification of Glycinin

This examples sets forth the modification of glycinin $A_{1a}B_{1b}$ to encode increased levels of essential amino acids. The glycinin $A_{1a}B_{1b}$ subunit amino acid sequence (SEQ ID NO: 1) is modified to substitute isoleucine residues for leucine residues at the amino acid positions: F43, F81, F117, F173, F330, F342, F351, F383, F399, F410, F415, F463, A19, A46, A49, A59, A124, A143, A221, A234, A319, A325, A332, A340, A349, A365, A370, A403, A429, or A452.

The substitutions are made using the GeneEditor™ in vitro Site-Directed Mutagenesis System (Promega Corporation, Madison, WI), according to the manufacturer's directions. Primers are designed to incorporate nucleotides encoding an isoleucine residue at positions F43, F81, F117, F173, F330, F342, F351, F383, F399, F410, F415, F463, A19, A46, A49, A59, A124, A143, A221, A234, A319, A325, A332, A340, A349, A365, A370, A403, A429, or A452.

Plasmid pMON65952 is used as a template in these reactions. Each mutagenic primer is designed to incorporate nucleotides encoding an essential amino acid residue at those positions listed above. Primers are obtained from Invitrogen (Invitrogen, Carlsbad, Calif), and are phosphorylated at the 5' terminus and purified by polyacrylamide gel electrophoresis.

Example 7

Preparation of Transgenic Plants and Seeds with Modified Glycinin $A_{1a}B_{1b}$ Genes.

Transformation vectors capable of introducing nucleic acid sequences encoding the modified glycinin $A_{1a}B_{1b}$ are designed, and generally contain one or more nucleic acid coding sequences of interest under the transcriptional control of 5' and 3' regulatory sequences. Such vectors comprise, operatively linked in sequence in the 5' to 3' direction, a promoter sequence that directs the transcription of a downstream structural nucleic acid sequence in a plant; a 5' non-translated leader sequence; a nucleic acid sequence that encodes a modified glycinin $A_{1a}B_{1b}$ sequence and a 3' non-translated region that provides a polyadenylation signal and termination signal.

Each of the modified glycinin $A_{1a}B_{1b}$ sequences are inserted into plant transformation vectors and transformed into plant tissue, e.g., soybean cotyledons. The transformed plant tissue is cultured in suitable selection and growth media to generate a transgenic plant containing the modified glycinin $A_{1a}B_{1b}$ sequence.

A variety of different methods can be employed to introduce such vectors into plant protoplasts, cells, callus tissue, leaf discs, meristems, and other plant tissues, to generate transgenic plants. The plant cells or plant tissue is transformed with the plant vector by *Agrobacterium*-mediated transformation, particle gun delivery, microinjection, electroporation, polyethylene glycol-mediated protoplast transformation, liposome-mediated transformation, etc. (reviewed in Potrykus, 1991). Plant cells or tissues are thus transformed with the plant vector containing the glycinin $A_{1a}B_{1b}$ sequence.

Transgenic plants are produced by transforming plant cells with a plant vector, as described above; selecting plant cells or tissues that have been transformed; regenerating plant cells that have been transformed to produce transgenic plants; and selecting the transgenic plants that express the desired glycinin $A_{1a}B_{1b}$ sequence.

The transgenic plants are screened for protein expression of the desired polypeptide having increased content of essential amino acids. The plants may also be screened for polypeptides having increased content of other essential amino acids, such as histidine, lysine, methionine, and phenylalanine.

Example 8

Confirmation that the Modified Glycinin $A_{1a}B_{1b}$, Modified to Contain 2 or More Isoleucine Residues, folds and Self-Assembles in *E. coli*.

This example sets forth confirmation of the protein structure from the expression of modified glycinin $A_{1a}B_{1b}$ clones. The assembly properties of the following modified forms of the protein (indicated by mutant ID number), each containing a different isoleucine substitution, are determined as described in Example 3. Western blot analysis of sucrose gradient fractions is carried out as in Example 3 using anti-FLAG antibody for each of mutants G1-4 through G13-2. Results indicate that 15 of the 18 forms self-assembled to form trimers.

TABLE 2

| Mutant ID | *E. coli* Assembly Results |
|---|---|
| g1-4 | Trimer |
| g2-5 | trimer |
| g3-5 | monomer |
| g3-6 | trimer |
| g3-7 | trimer |
| g3-8 | protein not detected |
| g3-9 | trimer |
| g4-1 | trimer |
| g5-2 | trimer |
| g6-4 | monomer |
| g6-7 | monomer |
| g7-1 | protein not detected |
| g7-2 | monomer & trimer |
| g7-3 | trimer |
| g7-7 | monomer & trimer |
| g8-16 | trimer |

TABLE 2-continued

| Mutant ID | *E. coli* Assembly Results |
|---|---|
| g10-5 | monomer & trimer |
| g10-10 | monomer |
| g12-1 | trimer |
| g13-2 | trimer |
| g15-2 | trimer |
| g17-1 | trimer |
| g17-2 | monomer & trimer |

REFERENCES

The following patents, patent applications, and references are specifically incorporated herein by reference in their entirety.

Ainley et al., *Plant Mol Biol.,* 14:949, 1990.

Altschul et al., *Journal of Molecular Biology,* 215:403–410, 1990.

Andreas et al., *Theor. Appl. Genet.,* 72:123–128, 1986.

Ausubel et al., *Current Protocols in Molecular Biology,* John Wiley and Sons, Inc., 1995.

Battraw and Hall, *Plant Sci.,* 86(2):191–202, 1992.

Back et al., *Plant Mol. Biol.,* 17:9, 1991.

Bauer et al., *Gene,* 37:73, 1985.

Becker and Guarente, In: Abelson and Simon (eds.), *Guide to Yeast Genetics and Molecular Biology, Methods Enzymol.,* vol. 194, pp. 182–187, Academic Press, Inc., NY.

Bennett and LaSure (eds.), *More Gene Manipulations in Fungi,* Academic Press, CA, 1991.

Bent et al., *Science,* 265:1856–1860, 1994.

Bergeron et al., *TIBS,* 19:124–128, 1994.

Bol et al., *Ann. Rev. Phytophathol,* 28:13–138, 1990.

Bowles, *Ann. Rev. Biochem,* 59:873-907, 1990.

Braun and Hemenway, *Seeds,* 4(6):735–744, 1992.

Broekaert et al., *Critical Reviews in Plant Sciences,* 16(3):297–323, 1997.

Bustos et al., *EMBO J.,* 10:1469–1479, 1991.

Castresana et al., *EMBO J.,* 7:1929–1936, 1988.

Capecchi, *Cell,* 22(2):479–488, 1980.

Cashmore et al., *Gen. Eng. of Plants,* Plenum Press, NY, 29–38, 1983.

Cerda-Olmedo et al., *J. Mol. Biol.,* 33:705-14 719, 1968.

Chau et al., *Science,* 244:174–181. 1989.

Christensen et al., *Plant Mol. Biol.,* 18:675,689, 1992.

Christou et al., *Plant Physiol.,* 87:671–674, 1988.

Christou et al., *Bio/Technology,* 9:957, 1991.

Clapp, *Clin, Perinatol.,* 20(1):155–168, 1993.

Costa et al., *Methods Mol. Biol.,* 57:31–44, 1996.

Craik, *BioTechniques,* 3:12–19, 1985.

Craig, *Science,* 260:1902–1903, 1993.

Curiel et al., *Hum. Gen. Ther.,* 3(2):147–154, 1992.

Davey et al., *Symp. Soc. Exp. Biol.,* 40:85–120, 1986.

Davey et al., *Plant Mol. Biol.,* 13(3):273–285, 1989.

De Kathen and Jacobsen, *Seeds Rep.,* 9(5):276–9, 1990.

Dellaporta et al., Stadler Symposium, 11:263–282, 1988.

De la Pena et al., *Nature,* 325:274, 1987.

Demolder et al., *J. Biotechnology,* 32:179–189, 1994.

Deng and Nickloff, *Anal. Biochem.,* 200:81, 1992.

Doyle et al., *J. Biol. Chem.,* 261:9228–9238, 1986.

Eglitis and Anderson, *Biotechniques,* 6(7):608–614, 1988.

Ellis et al., *Proc. Natl. Acad. Sci.* (*U.S.A.*), 92:4185, 1995.

Enderlin and Ogrydziak, *Yeast,* 10:67–79, 1994.

Feinbaum et al., *Mol. Gen. Genet.,* 226:449–456, 1991.

Fiedler et al., *Plant Molecular Biology,* 22:669–679, 1993.

Fitchen and Beachy, *Ann. Rev. Microbiol.,* 47:739–763, 1993.

Fraley et al., *Proc. Natl. Acad. Sci.* (*U.S.A.*), 80:4803, 1983.

Frits Eckstein et al., *Nucleic Acids Research,* 10:6487–6497, 1982.

Fromm et al., *Proc. Natl. Acad. Sci.* (*U.S.A.*), 82(17): 5824–5828, 1985.

Fromm et al., *Bio/Technology,* 8:833, 1990.

Fuller et al., *Proc. Natl. Acad. Sci.* (*U.S.A.*), 86:1434–1438, 1989.

Fynan et al., *Proc. Natl. Acad. Sci.* (*U.S.A.*), 90(24): 11478–11482, 1993.

Gasser and Fraley, *Science,* 244:1293, 1989.

Gething and Sambrook, *Nature,* 355:33–45, 1992.

Glick et al., *Methods in Plant Molecular Biology and Biotechnology,* CRC Press, Boca Raton, FL, 1993.

Goossens et al., *Eur. J. Biochem.,* 225:787–95, 1994.

Goossens et al., *Plant Physiol.,* 120:1095–1104, 1999.

Gordon-Kamm et al., *Seeds,* 2:603, 1990.

Graham and Van der Eb, *Virology,* 54(2):536–539, 1973.

Grant et al., *Seeds Rep.,* 15(3/4):254–258 1995.

Grant et al., *Science,* 269:843–846, 1995.

Greener et al., *Mol. Biotechnol.,* 7:189–195, 1997.

Guerola et al., *Nature New Biol.,* 230:122–125, 1971.

Harlow and Lane, In: *Antibodies: A Laboratory Manual,* Cold Spring Harbor Press, Cold Spring Harbor, NY, 1988.

Hartl et al., *TIBS,* 19:20–25, 1994.

Hershey and Stoner, *Plant Mol. Biol.,* 17:679–690, 1991.

Hess, *Intern Rev. Cytol.,* 107:367, 1987.

Hinchee et al., *Bio/Technology,* 6:915–922, 1988.

Hinnen et al., *Proc. Natl. Acad. Sci.* (*U.S.A.*), 75:1920, 1978.

Horsch et al., *Science,* 227:1229–1231, 1985.

Ikatu et al., *Bio/Technol.,* 8:241–242, 1990.

Ito et al., *J. Bacteriology,* 153:163, 1983.

Jarai and Buxton, *Current Genetics,* 26:2238–2244, 1994.

Jefferson (I), *Plant Mol. Biol, Rep.,* 5:387–405, 1987.

Jefferson (II) et al., *EMBO* J., 6:3901–3907, 1987.

Johnston and Tang, *Methods Cell Biol.,* 43(A):353–365, 1994.

Jones et al., *Science,* 266:789–793, 1994.

Julius et al., *Cell,* 32:839–852, 1983.

Julius et al., *Cell,* 37:1075–1089, 1984.

Kares et al., *Plant Mol. Biol.,* 15:905, 1990.

Katz et al., *J. Gen. Microbiol.,* 129:2703–2714, 1983.

Kawasaki, In: *PCR™ Protocols, A Guide to Methods and Applications,* Innis et al., (eds.), Academic Press, San Diego, CA, 21–27, 1990.

Kay et al., *Science,* 236:1299, 1987.

Keller et al. *EMBO L.,* 8:1309–1314, 1989.

Knutzon et al., *Proc. Natl. Acad. Sci.* (*U.S.A.*), 89:2624–2628, 1992.

Koziel et al., *Bio/Technology,* 11:194, 1993.

Kridl et al., *Seed Sci. Res.,* 1:209, 1991.

Kuby, "Immunology", 2d Edition,. W.H. Freeman and Company, NY, 1994.

Kudla et al., *EMBO,* 9:1355–1364, 1990.

Kuhlemeier et al., *Seeds,* 1:471, 1989.

Kunkel, *Proc. Natl. Acad. Sci.* (*U.S.A.*), 82:488–492, 1985.

Kyte and Doolittle, *J. Mol. Biol.,* 157:105–132, 1982.

Lam and Chua, *J. Biol. Chem.,* 266:17131–17135, 1990.

Lam and Chua, *Science,* 248:471, 1991.

Laemmli, *Nature,* 227:680–685, 1970.

Lioi and Bollini, *Bean Improvement Cooperative,* 32:28, 1989.

Lipman and Pearson, *Science,* 227:1435–1441, 1985.

Lindstrom et al., *Developmental Genetics,* 11:160, 1990.

Linthorst, *Crit. Rev. Plant Sci.,* 10:123–150, 1991.

Logemann et al., *Seeds,* 1:151–158, 1989.

Lu et al., *J. Exp. Med.,* 178(6):2089–2096, 1993.

Luo et al., *Plant Mol Biol. Reporter,* 6:165, 1988.

MacKenzie et al., *Journal of Gen. Microbiol.,* 139:2295–2307, 1993.

Mahadevan et al., *J. Animal Sci.,* 50:723–728, 1980.

Malardier et al., *Gene,* 78:147–156, 1989.

Maloy et al., "Microbial Genetics" 2$^{nd}$ Edition,, Jones and Barlett Publishers, Boston, MA, 1994.

Mandel et al., *Plant Mol. Biol.,* 29:995–1004, 1995.

Marraccini et al., *Plant Physiol. Biochem.* (*Paris*), 37(4): 273–282, 1999.

McCabe et al., *Biotechnolgy,* 6:923, 1988.

McElroy et al., *Seeds,* 2:163–171, 1990.

Needleman and Wunsch, *Journal of Molecular Biology,* 48:443–453, 1970.

Neuhaus et al., *Theor. Appl. Genet.,* 75:30, 1987.

Odell et al., *Nature,* 313:810, 1985.

Osborn et al., *Theor. Appl. Genet.,* 71:847–55, 1986.

Osuna et al., *Critical Reviews In Microbiology,* 20:107–116, 1994.

Ou-Lee et al., *Proc. Natl. Acad. Sci* (*U.S.A.*), 83:6815, 1986.

Ow et al., *Science,* 234:856–859, 1986.

Pearson and Lipman, *Proc. Natl. Acad. Sci.* (*U.S.A.*), 85:2444–2448, 1988.

Pearson, "Rapid and Sensitive Sequence Comparison with FASTP and FASTA". In *Methods in Enzymology,* (R. Doolittle, ed.), 183, 63–98, Academic Press, San Diego, CA, 1990.

Pearson, *Protein Science,* 4:1145–1160, 1995.

Pena et al., *Nature,* 325:274, 1987.

Perak et al., *Bio/Technology,* 8:939–943, 1990.

Perlak et al., *Plant Molecular Biology,* 22:313–321, 1993.

Pesole et al., *BioTechniques,* 25:112–123, 1998.

Poszkowski et al., *EMBO J.,* 3:2719, 1989.

Potrykus et al., *Ann. Rev. Plant Physiol. Plant Mol. Biol.,* 42:205, 1991.

Potrykus et al., *Mol. Gen. Genet.,* 199:183–188, 1985.

Puig and Gilbert, *J. Biol. Chem.,* 269:7764–7771, 1994.

Pyee et al., *Plant J.,* 7:49–59, 1995.

Rhodes et al., *Science,* 240:204, 1988.

Richins et al., *Nucleic Acids Res.,* 20:8451, 1987.

Robinson et al., *Bio/Technology,* 1:381–384, 1994.

Rodriguez et al., Vectors: A Survey of Molecular Cloning Vectors and Their Uses, Butterworths, Boston, MA, 1988.

Rogan and Bessman, *J. Bacteriol.,* 103:622–633, 1970.

Rogers et al., *Meth. In Enzymol,* 153:253–277, 1987.

Samac et al., *Seeds,* 3:1063–1072, 1991.

Sambrook et al., *Molecular Cloning: A Laboratory Manual,* Second Edition, Cold Spring Harbor Laboratory Press, Cold Spring Harbor, NY, 1989.

Schroeder et al., *Plant J.,* 2:161–172, 1992.

Schroeder et al., *Plant Physiol.,* 101(3):751–757, 1993.

Schulze-Lefert et al., *EMBO J.,* 8:651, 1989.

Sequence Analysis Software Package Manual (Version 1.0; Genetics Computer Group, Inc., University of Wisconsin Biotechnology Center, Madison, WI)

Simpson, *Science,* 233:34, 1986.

Singer and Kusmierek, *Ann. Rev. Biochem.,* 52:655–693, 1982.

Slighton and Beachy, *Planta,* 172:356, 1987.

Smith et al., In: *Genetic Engineering: Principles and Methods,* Setlow et al., (eds.), Plenum Press, NY, 1–32, 1981.

Smith and Waterman, *Advances in Applied Mathematics,* 2:482–489, 1981.

Smith et al., *Nucleic Acids Research,* 11:2205–2220, 1983.

Somers et al., *Bio/Technology,* 10:1589, 1992.

Stalker et al., *J. Biol. Chem.,* 263:6310–6314, 1988.

Sutcliffe et al., *Proc. Natl. Acad. Sci.* (*U.S.A.*), 75:3737–3741, 1978.

Thillet et al., *J. Biol. Chem.,* 263:12500–12508, 1988.

Vandeyar et al,. *Gene,* 65:129–133, 1988.

Van Tunen et al., *EMBO J.,* 7:1257, 1988.

Vasil, *Biotechnology,* 6:397, 1988.

Vasil et al., *Bio/Technology,* 10:667, 1992.

Verdier, *Yeast,* 6:271–297, 1990.

Vodkin et al., *Cell,* 34:1023, 1983.

Vogel et al., *J. Cell Biochem.,* (*Suppl*) 13D:312, 1989.

Wagner et al., *Proc. Natl. Acad. Sci.* (*U.S.A.*), 89(13): 6099–6103, 1992.

Wallace et al., *British J. Nutrition,* 50:345–355, 1983.

Wang and Tsou, *FASEB Journal,* 7:1515–1517, 1993.

Watkins, *Handbook of Insecticide Dust Diluents and Carriers,* Second Edition, Darland Books, Caldwell, NJ Weissbach and Weissbach, *Methods for Plant Molecular Biology,* (eds.), Academic Press, Inc., San Diego, CA, 1988.

Weisshaar et al., *EMBO J.,* 10:1777–1786, 1991.

Wenzler et al., *Plant Mol. Biol.,* 12:41–50, 1989.

Whitham et al., *Cell,* 78:1101–1115, 1994.

Williams et al., *Biotechnology,* 10:540–543, 1992.

Winnacker-Kuchler, *Chemical Technology,* 4$^{th}$ Ed., Vol. 7, Hanser Verlag, Munich, 1986.

Wolf et al., *Compu. Appl. Biosci.,* 4(1):187–91, 1988.

Wong and Neumann, *Biochim, Biophys. Res. Commun.,* 107(2):584–587, 1982.

Wu et al., *Seeds,* 7(9):1357–1368, 1995.

Yang et al., *Proc. Natl. Acad. Sci.* (*U.S.A.*), 87:4144–48, 1990.

Yamaguchi-Shinozaki et al., *Plant Mol. Biol.,* 15:905, 1990.

Yelton et al., *Proc. Natl. Acad. Sci.* (*U.S.A.*), 81:1470–1474, 1984.

Zatloukal et al., *Ann. N.Y. Acad. Sci.,* 660:136–153, 1992.

Zhang and Wu, *Theor. Appl. Genet.,* 76:835, 1988.

Zhou et al., *Methods in Enzymology,* 101:433, 1983.

Zukowsky et al., *Proc. Natl. Acad. Sci.* (*U.S.A.*), 80:1101–1105, 1983.

U.S. Pat. Nos. 3,959,493; 4,533,557; 4,554,101; 4,683,195; 4,683,202; 4,713,245; 4,757,011; 4,769,061; 4,826,694; 4,940,835; 4,957,748; 4,971,908; 5,100,679; 5,219,596; 5,384,253; 5,689,052; 5,936,069; 6,005,076; 6,146,669; and 6,156,227.

European Applications 0 154 204; 0 218 571; 0 238 023; 0 255 378; and 0 385 962.

SEQUENCE LISTING

```
<160> NUMBER OF SEQ ID NOS: 54

<210> SEQ ID NO 1
<211> LENGTH: 476
<212> TYPE: PRT
<213> ORGANISM: Glycine max

<400> SEQUENCE: 1

Phe Ser Ser Arg Glu Gln Pro Gln Gln Asn Glu Cys Gln Ile Gln Lys
1               5                   10                  15

Leu Asn Ala Leu Lys Pro Asp Asn Arg Ile Glu Ser Glu Gly Gly Leu
            20                  25                  30

Ile Glu Thr Trp Asn Pro Asn Asn Lys Pro Phe Gln Cys Ala Gly Val
        35                  40                  45

Ala Leu Ser Arg Cys Thr Leu Asn Arg Asn Ala Leu Arg Arg Pro Ser
    50                  55                  60

Tyr Thr Asn Gly Pro Gln Glu Ile Tyr Ile Gln Gln Gly Lys Gly Ile
65                  70                  75                  80

Phe Gly Met Ile Tyr Pro Gly Cys Pro Ser Thr Phe Glu Glu Pro Gln
```

-continued

```
                85                  90                  95

Gln Pro Gln Gln Arg Gly Gln Ser Ser Arg Pro Gln Asp Arg His Gln
            100                 105                 110

Lys Ile Tyr Asn Phe Arg Glu Gly Asp Leu Ile Ala Val Pro Thr Gly
        115                 120                 125

Val Ala Trp Trp Met Tyr Asn Asn Glu Asp Thr Pro Val Val Ala Val
    130                 135                 140

Ser Ile Ile Asp Thr Asn Ser Leu Glu Asn Gln Leu Asp Gln Met Pro
145                 150                 155                 160

Arg Arg Phe Tyr Leu Ala Gly Asn Gln Glu Gln Glu Phe Leu Lys Tyr
                165                 170                 175

Gln Gln Glu Gln Gly Gly His Gln Ser Gln Lys Gly Lys His Gln Gln
            180                 185                 190

Glu Glu Glu Asn Glu Gly Gly Ser Ile Leu Ser Gly Phe Thr Leu Glu
        195                 200                 205

Phe Leu Glu His Ala Phe Ser Val Asp Lys Gln Ile Ala Lys Asn Leu
    210                 215                 220

Gln Gly Glu Asn Glu Gly Glu Asp Lys Gly Ala Ile Val Thr Val Lys
225                 230                 235                 240

Gly Gly Leu Ser Val Ile Lys Pro Pro Thr Asp Glu Gln Gln Gln Arg
                245                 250                 255

Pro Gln Glu Glu Glu Glu Glu Glu Glu Asp Glu Lys Pro Gln Cys Lys
            260                 265                 270

Gly Lys Asp Lys His Cys Gln Arg Pro Arg Gly Ser Gln Ser Lys Ser
        275                 280                 285

Arg Arg Asn Gly Ile Asp Glu Thr Ile Cys Thr Met Arg Leu Arg His
    290                 295                 300

Asn Ile Gly Gln Thr Ser Ser Pro Asp Ile Tyr Asn Pro Gln Ala Gly
305                 310                 315                 320

Ser Val Thr Thr Ala Thr Ser Leu Asp Phe Pro Ala Leu Ser Trp Leu
                325                 330                 335

Arg Leu Ser Ala Glu Phe Gly Ser Leu Arg Lys Asn Ala Met Phe Val
            340                 345                 350

Pro His Tyr Asn Leu Asn Ala Asn Ser Ile Ile Tyr Ala Leu Asn Gly
        355                 360                 365

Arg Ala Leu Ile Gln Val Val Asn Cys Asn Gly Glu Arg Val Phe Asp
    370                 375                 380

Gly Glu Leu Gln Glu Gly Arg Val Leu Ile Val Pro Gln Asn Phe Val
385                 390                 395                 400

Val Ala Ala Arg Ser Gln Ser Asp Asn Phe Glu Tyr Val Ser Phe Lys
                405                 410                 415

Thr Asn Asp Thr Pro Met Ile Gly Thr Leu Ala Gly Ala Asn Ser Leu
            420                 425                 430

Leu Asn Ala Leu Pro Glu Glu Val Ile Gln His Thr Phe Asn Leu Lys
        435                 440                 445

Ser Gln Gln Ala Arg Gln Ile Lys Asn Asn Asn Pro Phe Lys Phe Leu
    450                 455                 460

Val Pro Pro Gln Glu Ser Gln Lys Arg Ala Val Ala
465                 470                 475
```

<210> SEQ ID NO 2
<211> LENGTH: 1431
<212> TYPE: DNA
<213> ORGANISM: Glycine max

<400> SEQUENCE: 2 ttcagttcca gagagcagcc tcagcaaaac gagtgccaga tccaaaaact caatgccctc 60 aaaccggata accgtataga gtcagaagga gggctcattg agacatggaa ccctaacaac 120 aagccattcc agtgtgccgg tgttgccctc tctcgctgca ccctcaaccg caacgccctt 180 cgtagacctt cctacaccaa cggtccccag gaaatctaca tccaacaagg taagggtatt 240 tttggcatga tatacccggg ttgtcctagc acatttgaag agcctcaaca acctcaacaa 300 agaggacaaa gcagcagacc acaagaccgt caccagaaga tctataactt cagagagggt 360 gatttgatcg cagtgcctac tggtgttgca tggtggatgt acaacaatga agacactcct 420 gttgttgccg tttctattat tgacaccaac agcttggaga accagctcga ccagatgcct 480 aggagattct atcttgctgg gaaccaagag caagagtttc taaaatatca gcaagagcaa 540 ggaggtcatc aaagccagaa aggaaagcat cagcaagaag aagaaaacga aggaggcagc 600 atattgagtg gcttcaccct ggaattcttg gaacatgcat tcagcgtgga caagcagata 660 gcgaaaaacc tacaaggaga gaacgaaggg gaagacaagg gagccattgt gacagtgaaa 720 ggaggtctga gcgtgataaa accacccacg gacgagcagc aacaaagacc ccaggaagag 780 gaagaagaag aagaggatga gaagccacag tgcaagggta aagacaaaca ctgccaacgc 840 ccccgaggaa gccaaagcaa aagcagaaga aatggcattg acgagaccat atgcaccatg 900 agacttcgcc acaacattgg ccagacttca tcacctgaca tctacaaccc tcaagccggt 960 agcgtcacaa ccgccaccag ccttgacttc ccagccctct cgtggctcag actcagtgct 1020 gagtttggat ctctccgcaa gaatgcaatg ttcgtgccac actacaacct gaacgcgaac 1080 agcataatat acgcattgaa tggacgggca ttgatacaag tggtgaattg caacggtgag 1140 agagtgtttg atggagagct gcaagaggga cgggtgctga tcgtgccaca aaactttgtg 1200 gtggctgcaa gatcacagag tgacaacttc gagtatgtgt cattcaagac caatgataca 1260 cccatgatcg gcactcttgc aggggcaaac tcattgttga acgcattacc agaggaagtg 1320 attcagcaca ctttcaacct aaaaagccag caggccaggc agataaagaa caacaaccct 1380 ttcaagttcc tggttccacc tcaggagtct cagaagagag ctgtggctta g 1431

<210> SEQ ID NO 3
<211> LENGTH: 18
<212> TYPE: DNA
<213> ORGANISM: Artificial
<220> FEATURE:
<223> OTHER INFORMATION: oligonucleotide primer

<400> SEQUENCE: 3 cactcatcag tcatcacc 18

<210> SEQ ID NO 4
<211> LENGTH: 18
<212> TYPE: DNA
<213> ORGANISM: Artificial
<220> FEATURE:
<223> OTHER INFORMATION: oligonucleotide primer

<400> SEQUENCE: 4 ggttgctagc actattgc 18

<210> SEQ ID NO 5
<211> LENGTH: 8
<212> TYPE: PRT

-continued

<213> ORGANISM: Artificial
<220> FEATURE:
<223> OTHER INFORMATION: FLAG epitope

<400> SEQUENCE: 5

Asp Tyr Leu Asp Asp Asp Asp Leu
1 5

<210> SEQ ID NO 6
<211> LENGTH: 24
<212> TYPE: DNA
<213> ORGANISM: Artificial
<220> FEATURE:
<223> OTHER INFORMATION: FLAG epitope

<400> SEQUENCE: 6 gactacaagg acgacgatga caag 24

<210> SEQ ID NO 7
<211> LENGTH: 54
<212> TYPE: DNA
<213> ORGANISM: Artificial
<220> FEATURE:
<223> OTHER INFORMATION: oligonucleotide primer

<400> SEQUENCE: 7 atagccatgg actacaagga cgacgatgac aagttcagtt ccagagagca gcct 54

<210> SEQ ID NO 8
<211> LENGTH: 17
<212> TYPE: DNA
<213> ORGANISM: Artificial
<220> FEATURE:
<223> OTHER INFORMATION: oligonucleotide primer

<400> SEQUENCE: 8 caggaaacag ctatgac 17

<210> SEQ ID NO 9
<211> LENGTH: 485
<212> TYPE: PRT
<213> ORGANISM: glycine max

<400> SEQUENCE: 9

Met Asp Tyr Lys Asp Asp Asp Asp Lys Phe Ser Ser Arg Glu Gln Pro
1 5 10 15

Gln Gln Asn Glu Cys Gln Ile Gln Lys Leu Asn Ala Leu Lys Pro Asp
20 25 30

Asn Arg Ile Glu Ser Glu Gly Gly Leu Ile Glu Thr Trp Asn Pro Asn
35 40 45

Asn Lys Pro Phe Gln Cys Ala Gly Val Ala Leu Ser Arg Cys Thr Leu
50 55 60

Asn Arg Asn Ala Leu Arg Arg Pro Ser Tyr Thr Asn Gly Pro Gln Glu
65 70 75 80

Ile Tyr Ile Gln Gln Gly Lys Gly Ile Phe Gly Met Ile Tyr Pro Gly
85 90 95

Cys Pro Ser Thr Phe Glu Glu Pro Gln Gln Pro Gln Gln Arg Gly Gln
100 105 110

Ser Ser Arg Pro Gln Asp Arg His Gln Lys Ile Tyr Asn Phe Arg Glu
115 120 125

Gly Asp Leu Ile Ala Val Pro Thr Gly Val Ala Trp Trp Met Tyr Asn
130 135 140

-continued

```
Asn Glu Asp Thr Pro Val Val Ala Val Ser Ile Ile Asp Thr Asn Ser
145                 150                 155                 160

Leu Glu Asn Gln Leu Asp Gln Met Pro Arg Arg Phe Tyr Leu Ala Gly
                165                 170                 175

Asn Gln Glu Gln Glu Phe Leu Lys Tyr Gln Gln Glu Gln Gly Gly His
            180                 185                 190

Gln Ser Gln Lys Gly Lys His Gln Gln Glu Glu Glu Asn Glu Gly Gly
        195                 200                 205

Ser Ile Leu Ser Gly Phe Thr Leu Glu Phe Leu Glu His Ala Phe Ser
    210                 215                 220

Val Asp Lys Gln Ile Ala Lys Asn Leu Gln Gly Glu Asn Glu Gly Glu
225                 230                 235                 240

Asp Lys Gly Ala Ile Val Thr Val Lys Gly Gly Leu Ser Val Ile Lys
                245                 250                 255

Pro Pro Thr Asp Glu Gln Gln Gln Arg Pro Gln Glu Glu Glu Glu Glu
            260                 265                 270

Glu Glu Asp Glu Lys Pro Gln Cys Lys Gly Lys Asp Lys His Cys Gln
        275                 280                 285

Arg Pro Arg Gly Ser Gln Ser Lys Ser Arg Arg Asn Gly Ile Asp Glu
    290                 295                 300

Thr Ile Cys Thr Met Arg Leu Arg His Asn Ile Gly Gln Thr Ser Ser
305                 310                 315                 320

Pro Asp Ile Tyr Asn Pro Gln Ala Gly Ser Val Thr Thr Ala Thr Ser
                325                 330                 335

Leu Asp Phe Pro Ala Leu Ser Trp Leu Arg Leu Ser Ala Glu Phe Gly
            340                 345                 350

Ser Leu Arg Lys Asn Ala Met Phe Val Pro His Tyr Asn Leu Asn Ala
        355                 360                 365

Asn Ser Ile Ile Tyr Ala Leu Asn Gly Arg Ala Leu Ile Gln Val Val
    370                 375                 380

Asn Cys Asn Gly Glu Arg Val Phe Asp Gly Glu Leu Gln Glu Gly Arg
385                 390                 395                 400

Val Leu Ile Val Pro Gln Asn Phe Val Val Ala Ala Arg Ser Gln Ser
                405                 410                 415

Asp Asn Phe Glu Tyr Val Ser Phe Lys Thr Asn Asp Thr Pro Met Ile
            420                 425                 430

Gly Thr Leu Ala Gly Ala Asn Ser Leu Leu Asn Ala Leu Pro Glu Glu
        435                 440                 445

Val Ile Gln His Thr Phe Asn Leu Lys Ser Gln Gln Ala Arg Gln Ile
    450                 455                 460

Lys Asn Asn Asn Pro Phe Lys Phe Leu Val Pro Pro Gln Glu Ser Gln
465                 470                 475                 480

Lys Arg Ala Val Ala
                485


<210> SEQ ID NO 10
<211> LENGTH: 1458
<212> TYPE: DNA
<213> ORGANISM: glycine max

<400> SEQUENCE: 10

atggactaca aggacgacga tgacaagttc agttccagag agcagcctca gcaaaacgag      60

tgccagatcc aaaaactcaa tgccctcaaa ccggataacc gtatagagtc agaaggaggg     120
```

-continued

```
ctcattgaga catggaaccc taacaacaag ccattccagt gtgccggtgt tgccctctct    180

cgctgcaccc tcaaccgcaa cgcccttcgt agaccttcct acaccaacgg tccccaggaa    240

atctacatcc aacaaggtaa gggtattttt ggcatgatat acccgggttg tcctagcaca    300

tttgaagagc ctcaacaacc tcaacaaaga ggacaaagca gcagaccaca agaccgtcac    360

cagaagatct ataacttcag agagggtgat ttgatcgcag tgcctactgg tgttgcatgg    420

tggatgtaca acaatgaaga cactcctgtt gttgccgttt ctattattga caccaacagc    480

ttggagaacc agctcgacca gatgcctagg agattctatc ttgctgggaa ccaagagcaa    540

gagtttctaa aatatcagca agagcaagga ggtcatcaaa gccagaaagg aaagcatcag    600

caagaagaag aaaacgaagg aggcagcata ttgagtggct tcaccctgga attcttggaa    660

catgcattca gcgtggacaa gcagatagcg aaaaacctac aaggagagaa cgaaggggaa    720

gacaagggag ccattgtgac agtgaaagga ggtctgagcg tgataaaacc acccacggac    780

gagcagcaac aaagacccca ggaagaggaa gaagaagaag aggatgagaa gccacagtgc    840

aagggtaaag acaaacactg ccaacgcccc cgaggaagcc aaagcaaaag cagaagaaat    900

ggcattgacg agaccatatg caccatgaga cttcgccaca acattggcca gacttcatca    960

cctgacatct acaaccctca agccggtagc gtcacaaccg ccaccagcct tgacttccca   1020

gccctctcgt ggctcagact cagtgctgag tttggatctc tccgcaagaa tgcaatgttc   1080

gtgccacact acaacctgaa cgcgaacagc ataatatacg cattgaatgg acgggcattg   1140

atacaagtgg tgaattgcaa cggtgagaga gtgtttgatg gagagctgca agagggacgg   1200

gtgctgatcg tgccacaaaa ctttgtggtg gctgcaagat cacagagtga caacttcgag   1260

tatgtgtcat tcaagaccaa tgatacaccc atgatcggca ctcttgcagg ggcaaactca   1320

ttgttgaacg cattaccaga ggaagtgatt cagcacactt tcaacctaaa aagccagcag   1380

gccaggcaga taaagaacaa caaccctttc aagttcctgg ttccacctca ggagtctcag   1440

aagagagctg tggcttag                                                 1458
```

<210> SEQ ID NO 11
<211> LENGTH: 19
<212> TYPE: DNA
<213> ORGANISM: artificial
<220> FEATURE:
<223> OTHER INFORMATION: olgonucleotide primer

<400> SEQUENCE: 11

```
ttcagttcca gagagcagc                                                 19
```

<210> SEQ ID NO 12
<211> LENGTH: 59
<212> TYPE: DNA
<213> ORGANISM: Artificial
<220> FEATURE:
<223> OTHER INFORMATION: oligonucleotide primer

<400> SEQUENCE: 12

```
acgcggatcc ctacttgtca tcgtcgtcct tgtagtcagc cacagctctc ttctgagac     59
```

<210> SEQ ID NO 13
<211> LENGTH: 485
<212> TYPE: PRT
<213> ORGANISM: glycine max

<400> SEQUENCE: 13

```
Met Phe Ser Ser Arg Glu Gln Pro Gln Gln Asn Glu Cys Gln Ile Gln
```

-continued

```
1               5                   10                  15

Lys Leu Asn Ala Leu Lys Pro Asp Asn Arg Ile Glu Ser Glu Gly Gly
            20                  25                  30

Leu Ile Glu Thr Trp Asn Pro Asn Asn Lys Pro Phe Gln Cys Ala Gly
        35                  40                  45

Val Ala Leu Ser Arg Cys Thr Leu Asn Arg Asn Ala Leu Arg Arg Pro
    50                  55                  60

Ser Tyr Thr Asn Gly Pro Gln Glu Ile Tyr Ile Gln Gln Gly Lys Gly
65                  70                  75                  80

Ile Phe Gly Met Ile Tyr Pro Gly Cys Pro Ser Thr Phe Glu Glu Pro
                85                  90                  95

Gln Gln Pro Gln Gln Arg Gly Gln Ser Ser Arg Pro Gln Asp Arg His
            100                 105                 110

Gln Lys Ile Tyr Asn Phe Arg Glu Gly Asp Leu Ile Ala Val Pro Thr
        115                 120                 125

Gly Val Ala Trp Trp Met Tyr Asn Asn Glu Asp Thr Pro Val Val Ala
    130                 135                 140

Val Ser Ile Ile Asp Thr Asn Ser Leu Glu Asn Gln Leu Asp Gln Met
145                 150                 155                 160

Pro Arg Arg Phe Tyr Leu Ala Gly Asn Gln Glu Gln Glu Phe Leu Lys
                165                 170                 175

Tyr Gln Gln Glu Gln Gly Gly His Gln Ser Gln Lys Gly Lys His Gln
            180                 185                 190

Gln Glu Glu Glu Asn Glu Gly Gly Ser Ile Leu Ser Gly Phe Thr Leu
        195                 200                 205

Glu Phe Leu Glu His Ala Phe Ser Val Asp Lys Gln Ile Ala Lys Asn
    210                 215                 220

Leu Gln Gly Glu Asn Glu Gly Glu Asp Lys Gly Ala Ile Val Thr Val
225                 230                 235                 240

Lys Gly Gly Leu Ser Val Ile Lys Pro Pro Thr Asp Glu Gln Gln Gln
                245                 250                 255

Arg Pro Gln Glu Glu Glu Glu Glu Glu Glu Asp Glu Lys Pro Gln Cys
            260                 265                 270

Lys Gly Lys Asp Lys His Cys Gln Arg Pro Arg Gly Ser Gln Ser Lys
        275                 280                 285

Ser Arg Arg Asn Gly Ile Asp Glu Thr Ile Cys Thr Met Arg Leu Arg
    290                 295                 300

His Asn Ile Gly Gln Thr Ser Ser Pro Asp Ile Tyr Asn Pro Gln Ala
305                 310                 315                 320

Gly Ser Val Thr Thr Ala Thr Ser Leu Asp Phe Pro Ala Leu Ser Trp
                325                 330                 335

Leu Arg Leu Ser Ala Glu Phe Gly Ser Leu Arg Lys Asn Ala Met Phe
            340                 345                 350

Val Pro His Tyr Asn Leu Asn Ala Asn Ser Ile Ile Tyr Ala Leu Asn
        355                 360                 365

Gly Arg Ala Leu Ile Gln Val Val Asn Cys Asn Gly Glu Arg Val Phe
    370                 375                 380

Asp Gly Glu Leu Gln Glu Gly Arg Val Leu Ile Val Pro Gln Asn Phe
385                 390                 395                 400

Val Val Ala Ala Arg Ser Gln Ser Asp Asn Phe Glu Tyr Val Ser Phe
                405                 410                 415

Lys Thr Asn Asp Thr Pro Met Ile Gly Thr Leu Ala Gly Ala Asn Ser
            420                 425                 430
```

```
Leu Leu Asn Ala Leu Pro Glu Glu Val Ile Gln His Thr Phe Asn Leu
        435                 440                 445

Lys Ser Gln Gln Ala Arg Gln Ile Lys Asn Asn Asn Pro Phe Lys Phe
    450                 455                 460

Leu Val Pro Pro Gln Glu Ser Gln Lys Arg Ala Val Ala Asp Tyr Lys
465                 470                 475                 480

Asp Asp Asp Asp Lys
                485


<210> SEQ ID NO 14
<211> LENGTH: 1458
<212> TYPE: DNA
<213> ORGANISM: glycine max

<400> SEQUENCE: 14

atgttcagtt ccagagagca gcctcagcaa aacgagtgcc agatccaaaa actcaatgcc     60

ctcaaaccgg ataaccgtat agagtcagaa ggagggctca ttgagacatg gaaccctaac    120

aacaagccat tccagtgtgc cggtgttgcc ctctctcgct gcaccctcaa ccgcaacgcc    180

cttcgtagac cttcctacac caacggtccc caggaaatct acatccaaca aggtaagggt    240

atttttggca tgatataccc gggttgtcct agcacatttg aagagcctca acaacctcaa    300

caaagaggac aaagcagcag accacaagac cgtcaccaga agatctataa cttcagagag    360

ggtgatttga tcgcagtgcc tactggtgtt gcatggtgga tgtacaacaa tgaagacact    420

cctgttgttg ccgtttctat tattgacacc aacagcttgg agaaccagct cgaccagatg    480

cctaggagat tctatcttgc tgggaaccaa gagcaagagt ttctaaaata tcagcaagag    540

caaggaggtc atcaaagcca gaaaggaaag catcagcaag aagaagaaaa cgaaggaggc    600

agcatattga gtggcttcac cctggaattc ttggaacatg cattcagcgt ggacaagcag    660

atagcgaaaa acctacaagg agagaacgaa ggggaagaca agggagccat tgtgacagtg    720

aaaggaggtc tgagcgtgat aaaaccaccc acggacgagc agcaacaaag accccaggaa    780

gaggaagaag aagaagagga tgagaagcca cagtgcaagg gtaaagacaa acactgccaa    840

cgcccccgag gaagccaaag caaaagcaga agaaatggca ttgacgagac catatgcacc    900

atgagacttc gccacaacat tggccagact tcatcacctg acatctacaa ccctcaagcc    960

ggtagcgtca caaccgccac cagccttgac ttcccagccc tctcgtggct cagactcagt   1020

gctgagtttg gatctctccg caagaatgca atgttcgtgc cacactacaa cctgaacgcg   1080

aacagcataa tatacgcatt gaatggacgg gcattgatac aagtggtgaa ttgcaacggt   1140

gagagagtgt ttgatggaga gctgcaagag ggacgggtgc tgatcgtgcc acaaaacttt   1200

gtggtggctg caagatcaca gagtgacaac ttcgagtatg tgtcattcaa gaccaatgat   1260

acacccatga tcggcactct tgcaggggca aactcattgt tgaacgcatt accagaggaa   1320

gtgattcagc acactttcaa cctaaaaagc cagcaggcca ggcagataaa gaacaacaac   1380

cctttcaagt tcctggttcc acctcaggag tctcagaaga gagctgtggc tgactacaag   1440

gacgacgatg acaagtag                                                 1458


<210> SEQ ID NO 15
<211> LENGTH: 477
<212> TYPE: PRT
<213> ORGANISM: glycine max

<400> SEQUENCE: 15
```

-continued

```
Met Phe Ser Ser Arg Glu Gln Pro Gln Gln Asn Glu Cys Gln Ile Gln
1               5                   10                  15

Lys Leu Asn Ala Leu Lys Pro Asp Asn Arg Ile Glu Ser Glu Gly Gly
            20                  25                  30

Leu Ile Glu Thr Trp Asn Pro Asn Asn Lys Pro Phe Gln Cys Ala Gly
        35                  40                  45

Val Ala Leu Ser Arg Cys Thr Leu Asn Arg Asn Ala Leu Arg Arg Pro
    50                  55                  60

Ser Tyr Thr Asn Gly Pro Gln Glu Ile Tyr Ile Gln Gln Gly Lys Gly
65                  70                  75                  80

Ile Phe Gly Met Ile Tyr Pro Gly Cys Pro Ser Thr Phe Glu Glu Pro
                85                  90                  95

Gln Gln Pro Gln Gln Arg Gly Gln Ser Ser Arg Pro Gln Asp Arg His
            100                 105                 110

Gln Lys Ile Tyr Asn Phe Arg Glu Gly Asp Leu Ile Ala Val Pro Thr
        115                 120                 125

Gly Val Ala Trp Trp Met Tyr Asn Asn Glu Asp Thr Pro Val Val Ala
    130                 135                 140

Val Ser Ile Ile Asp Thr Asn Ser Leu Glu Asn Gln Leu Asp Gln Met
145                 150                 155                 160

Pro Arg Arg Phe Tyr Leu Ala Gly Asn Gln Glu Gln Glu Phe Leu Lys
                165                 170                 175

Tyr Gln Gln Glu Gln Gly Gly His Gln Ser Gln Lys Gly Lys His Gln
            180                 185                 190

Gln Glu Glu Glu Asn Glu Gly Gly Ser Ile Leu Ser Gly Phe Thr Leu
        195                 200                 205

Glu Phe Leu Glu His Ala Phe Ser Val Asp Lys Gln Ile Ala Lys Asn
    210                 215                 220

Leu Gln Gly Glu Asn Glu Gly Glu Asp Lys Gly Ala Ile Val Thr Val
225                 230                 235                 240

Lys Gly Gly Leu Ser Val Ile Lys Pro Pro Thr Asp Glu Gln Gln Gln
                245                 250                 255

Arg Pro Gln Glu Glu Glu Glu Glu Glu Glu Asp Glu Lys Pro Gln Cys
            260                 265                 270

Lys Gly Lys Asp Lys His Cys Gln Arg Pro Arg Gly Ser Gln Ser Lys
        275                 280                 285

Ser Arg Arg Asn Gly Ile Asp Glu Thr Ile Cys Thr Met Arg Leu Arg
    290                 295                 300

His Asn Ile Gly Gln Thr Ser Ser Pro Asp Ile Tyr Asn Pro Gln Ala
305                 310                 315                 320

Gly Ser Val Thr Thr Ala Thr Ser Leu Asp Phe Pro Ala Leu Ser Trp
                325                 330                 335

Leu Arg Leu Ser Ala Glu Phe Gly Ser Leu Arg Lys Asn Ala Met Phe
            340                 345                 350

Val Pro His Tyr Asn Leu Asn Ala Asn Ser Ile Ile Tyr Ala Leu Asn
        355                 360                 365

Gly Arg Ala Leu Ile Gln Val Val Asn Cys Asn Gly Glu Arg Val Phe
    370                 375                 380

Asp Gly Glu Leu Gln Glu Gly Arg Val Leu Ile Val Pro Gln Asn Phe
385                 390                 395                 400

Val Val Ala Ala Arg Ser Gln Ser Asp Asn Phe Glu Tyr Val Ser Phe
                405                 410                 415

Lys Thr Asn Asp Thr Pro Met Ile Gly Thr Leu Ala Gly Ala Asn Ser
```

-continued

```
            420                 425                 430

Leu Leu Asn Ala Leu Pro Glu Glu Val Ile Gln His Thr Phe Asn Leu
        435                 440                 445

Lys Ser Gln Gln Ala Arg Gln Ile Lys Asn Asn Asn Pro Phe Lys Phe
    450                 455                 460

Leu Val Pro Pro Gln Glu Ser Gln Lys Arg Ala Val Ala
465                 470                 475


<210> SEQ ID NO 16
<211> LENGTH: 1434
<212> TYPE: DNA
<213> ORGANISM: glycine max

<400> SEQUENCE: 16

atgttcagtt ccagagagca gcctcagcaa aacgagtgcc agatccaaaa actcaatgcc     60

ctcaaaccgg ataaccgtat agagtcagaa ggagggctca ttgagacatg gaaccctaac    120

aacaagccat tccagtgtgc cggtgttgcc ctctctcgct gcaccctcaa ccgcaacgcc    180

cttcgtagac cttcctacac caacggtccc caggaaatct acatccaaca aggtaagggt    240

atttttggca tgatataccc gggttgtcct agcacatttg aagagcctca acaacctcaa    300

caaagaggac aaagcagcag accacaagac cgtcaccaga agatctataa cttcagagag    360

ggtgatttga tcgcagtgcc tactggtgtt gcatggtgga tgtacaacaa tgaagacact    420

cctgttgttg ccgtttctat tattgacacc aacagcttgg agaaccagct cgaccagatg    480

cctaggagat tctatcttgc tgggaaccaa gagcaagagt ttctaaaata tcagcaagag    540

caaggaggtc atcaaagcca gaaaggaaag catcagcaag aagaagaaaa cgaaggaggc    600

agcatattga gtggcttcac cctggaattc ttggaacatg cattcagcgt ggacaagcag    660

atagcgaaaa acctacaagg agagaacgaa ggggaagaca agggagccat tgtgacagtg    720

aaaggaggtc tgagcgtgat aaaaccaccc acggacgagc agcaacaaag accccaggaa    780

gaggaagaag aagaagagga tgagaagcca cagtgcaagg gtaaagacaa acactgccaa    840

cgcccccgag gaagccaaag caaaagcaga agaaatggca ttgacgagac catatgcacc    900

atgagacttc gccacaacat tggccagact tcatcacctg acatctacaa ccctcaagcc    960

ggtagcgtca caaccgccac cagccttgac ttcccagccc tctcgtggct cagactcagt   1020

gctgagtttg gatctctccg caagaatgca atgttcgtgc cacactacaa cctgaacgcg   1080

aacagcataa tatacgcatt gaatggacgg gcattgatac aagtggtgaa ttgcaacggt   1140

gagagagtgt ttgatggaga gctgcaagag ggacgggtgc tgatcgtgcc acaaaacttt   1200

gtggtggctg caagatcaca gagtgacaac ttcgagtatg tgtcattcaa gaccaatgat   1260

acacccatga tcggcactct tgcaggggca aactcattgt tgaacgcatt accagaggaa   1320

gtgattcagc acactttcaa cctaaaaagc cagcaggcca ggcagataaa gaacaacaac   1380

cctttcaagt tcctggttcc acctcaggag tctcagaaga gagctgtggc ttag         1434


<210> SEQ ID NO 17
<211> LENGTH: 19
<212> TYPE: DNA
<213> ORGANISM: Artificial
<220> FEATURE:
<223> OTHER INFORMATION: oligonucleotide primer

<400> SEQUENCE: 17

ctcaatgcca tcaaaccgg                                                  19
```

-continued

<210> SEQ ID NO 18
<211> LENGTH: 28
<212> TYPE: DNA
<213> ORGANISM: Artificial
<220> FEATURE:
<223> OTHER INFORMATION: oligonucleotide primer

<400> SEQUENCE: 18 gacaccaaca gcattgagaa ccagctcg 28

<210> SEQ ID NO 19
<211> LENGTH: 32
<212> TYPE: DNA
<213> ORGANISM: Artificial
<220> FEATURE:
<223> OTHER INFORMATION: oligonucleotide primer

<400> SEQUENCE: 19 gcataatata cgcaattaat ggacgggcat tg 32

<210> SEQ ID NO 20
<211> LENGTH: 28
<212> TYPE: DNA
<213> ORGANISM: Artificial
<220> FEATURE:
<223> OTHER INFORMATION: oligonucleotide primer

<400> SEQUENCE: 20 gagagggtga tattatcgca gtgcctac 28

<210> SEQ ID NO 21
<211> LENGTH: 20
<212> TYPE: DNA
<213> ORGANISM: Artificial
<220> FEATURE:
<223> OTHER INFORMATION: oligonucleotide primer

<400> SEQUENCE: 21 cttcccagcc atctcgtggc 20

<210> SEQ ID NO 22
<211> LENGTH: 23
<212> TYPE: DNA
<213> ORGANISM: Artificial
<220> FEATURE:
<223> OTHER INFORMATION: oligonucleotide primer

<400> SEQUENCE: 22 gtttggatct atccgcaaga atg 23

<210> SEQ ID NO 23
<211> LENGTH: 25
<212> TYPE: DNA
<213> ORGANISM: Artificial
<220> FEATURE:
<223> OTHER INFORMATION: oligonucleotide primer

<400> SEQUENCE: 23 ccagatccaa aaaatcaatg ccctc 25

<210> SEQ ID NO 24
<211> LENGTH: 20
<212> TYPE: DNA
<213> ORGANISM: Artificial
<220> FEATURE:
<223> OTHER INFORMATION: oligonucleotide primer -continued

<400> SEQUENCE: 24 gaaggaggga tcattgagac 20

<210> SEQ ID NO 25
<211> LENGTH: 28
<212> TYPE: DNA
<213> ORGANISM: Artificial
<220> FEATURE:
<223> OTHER INFORMATION: oligonucleotide primer

<400> SEQUENCE: 25 gaatggacgg gcaattatac aagtggtg 28

<210> SEQ ID NO 26
<211> LENGTH: 20
<212> TYPE: DNA
<213> ORGANISM: Artificial
<220> FEATURE:
<223> OTHER INFORMATION: oligonucleotide primer

<400> SEQUENCE: 26 ggtgttgcca tctctcgctg 20

<210> SEQ ID NO 27
<211> LENGTH: 20
<212> TYPE: DNA
<213> ORGANISM: Artificial
<220> FEATURE:
<223> OTHER INFORMATION: oligonucleotide primer

<400> SEQUENCE: 27 gccaccagca ttgacttccc 20

<210> SEQ ID NO 28
<211> LENGTH: 28
<212> TYPE: DNA
<213> ORGANISM: Artificial
<220> FEATURE:
<223> OTHER INFORMATION: oligonucleotide primer

<400> SEQUENCE: 28 gtttgatgga gagattcaag agggacgg 28

<210> SEQ ID NO 29
<211> LENGTH: 21
<212> TYPE: DNA
<213> ORGANISM: Artificial
<220> FEATURE:
<223> OTHER INFORMATION: oligonucleotide primer

<400> SEQUENCE: 29 cgctgcacca tcaaccgcaa c 21

<210> SEQ ID NO 30
<211> LENGTH: 22
<212> TYPE: DNA
<213> ORGANISM: Artificial
<220> FEATURE:
<223> OTHER INFORMATION: oligonucleotide primer

<400> SEQUENCE: 30 caccatgaga attcgccaca ac 22

<210> SEQ ID NO 31

-continued

<211> LENGTH: 20
<212> TYPE: DNA
<213> ORGANISM: Artificial
<220> FEATURE:
<223> OTHER INFORMATION: oligonucleotide primer

<400> SEQUENCE: 31 gtggctcaga atcagtgctg 20

<210> SEQ ID NO 32
<211> LENGTH: 20
<212> TYPE: DNA
<213> ORGANISM: Artificial
<220> FEATURE:
<223> OTHER INFORMATION: oligonucleotide primer

<400> SEQUENCE: 32 cgcaacgcca ttcgtagacc 20

<210> SEQ ID NO 33
<211> LENGTH: 28
<212> TYPE: DNA
<213> ORGANISM: Artificial
<220> FEATURE:
<223> OTHER INFORMATION: oligonucleotide primer

<400> SEQUENCE: 33 gagcaagagt ttataaaata tcagcaag 28

<210> SEQ ID NO 34
<211> LENGTH: 20
<212> TYPE: DNA
<213> ORGANISM: Artificial
<220> FEATURE:
<223> OTHER INFORMATION: oligonucleotide primer

<400> SEQUENCE: 34 ctctcgtgga tcagactcag 20

<210> SEQ ID NO 35
<211> LENGTH: 30
<212> TYPE: DNA
<213> ORGANISM: Artificial
<220> FEATURE:
<223> OTHER INFORMATION: oligonucleotide primer

<400> SEQUENCE: 35 gagggacggg tgattatcgt gccacaaaac 30

<210> SEQ ID NO 36
<211> LENGTH: 31
<212> TYPE: DNA
<213> ORGANISM: Artificial
<220> FEATURE:
<223> OTHER INFORMATION: oligonucleotide primer

<400> SEQUENCE: 36 ccctttcaag ttcattgttc cacctcagga g 31

<210> SEQ ID NO 37
<211> LENGTH: 22
<212> TYPE: DNA
<213> ORGANISM: Artificial
<220> FEATURE:
<223> OTHER INFORMATION: oligonucleotide primer

<400> SEQUENCE: 37

-continued gagattctat attgctggga ac 22

<210> SEQ ID NO 38
<211> LENGTH: 28
<212> TYPE: DNA
<213> ORGANISM: Artificial
<220> FEATURE:
<223> OTHER INFORMATION: oligonucleotide primer

<400> SEQUENCE: 38 ggaggcagca taatcagtgg cttcaccc 28

<210> SEQ ID NO 39
<211> LENGTH: 27
<212> TYPE: DNA
<213> ORGANISM: Artificial
<220> FEATURE:
<223> OTHER INFORMATION: oligonucleotide primer

<400> SEQUENCE: 39 gtggcttcac catcgaattc ttggaac 27

<210> SEQ ID NO 40
<211> LENGTH: 29
<212> TYPE: DNA
<213> ORGANISM: Artificial
<220> FEATURE:
<223> OTHER INFORMATION: oligonucleotide primer

<400> SEQUENCE: 40 ccctggaatt catagaacat gcattcagc 29

<210> SEQ ID NO 41
<211> LENGTH: 32
<212> TYPE: DNA
<213> ORGANISM: Artificial
<220> FEATURE:
<223> OTHER INFORMATION: oligonucleotide primer

<400> SEQUENCE: 41 gggcaaactc attgattaac gcattaccag ag 32

<210> SEQ ID NO 42
<211> LENGTH: 32
<212> TYPE: DNA
<213> ORGANISM: Artificial
<220> FEATURE:
<223> OTHER INFORMATION: oligonucleotide primer

<400> SEQUENCE: 42 gtgaaaggag gtattagcgt gataaaacca cc 32

<210> SEQ ID NO 43
<211> LENGTH: 21
<212> TYPE: DNA
<213> ORGANISM: Artificial
<220> FEATURE:
<223> OTHER INFORMATION: oligonucleotide primer

<400> SEQUENCE: 43 gatcggcact attgcagggg c 21

<210> SEQ ID NO 44
<211> LENGTH: 29
<212> TYPE: DNA

-continued

<213> ORGANISM: Artificial
<220> FEATURE:
<223> OTHER INFORMATION: oligonucleotide primer

<400> SEQUENCE: 44 ggggcaaact caaatttgaa cgcattacc 29

<210> SEQ ID NO 45
<211> LENGTH: 29
<212> TYPE: DNA
<213> ORGANISM: Artificial
<220> FEATURE:
<223> OTHER INFORMATION: oligonucleotide primer

<400> SEQUENCE: 45 cattgttgaa cgcaatacca gaggaagtg 29

<210> SEQ ID NO 46
<211> LENGTH: 26
<212> TYPE: DNA
<213> ORGANISM: Artificial
<220> FEATURE:
<223> OTHER INFORMATION: oligonucleotide primer

<400> SEQUENCE: 46 gtaagggtat tattggcatg atatac 26

<210> SEQ ID NO 47
<211> LENGTH: 23
<212> TYPE: DNA
<213> ORGANISM: Artificial
<220> FEATURE:
<223> OTHER INFORMATION: oligonucleotide primer

<400> SEQUENCE: 47 gatctataac atcagagagg gtg 23

<210> SEQ ID NO 48
<211> LENGTH: 34
<212> TYPE: DNA
<213> ORGANISM: Artificial
<220> FEATURE:
<223> OTHER INFORMATION: oligonucleotide primer

<400> SEQUENCE: 48 gttgcatggt ggatgatcaa caatgaagac actc 34

<210> SEQ ID NO 49
<211> LENGTH: 23
<212> TYPE: DNA
<213> ORGANISM: Artificial
<220> FEATURE:
<223> OTHER INFORMATION: oligonucleotide primer

<400> SEQUENCE: 49 ccagccttga catcccagcc ctc 23

<210> SEQ ID NO 50
<211> LENGTH: 25
<212> TYPE: DNA
<213> ORGANISM: Artificial
<220> FEATURE:
<223> OTHER INFORMATION: oligonucleotide primer

<400> SEQUENCE: 50 gaatgcaatg atcgtgccac actac 25

-continued

```
<210> SEQ ID NO 51
<211> LENGTH: 34
<212> TYPE: DNA
<213> ORGANISM: Artificial
<220> FEATURE:
<223> OTHER INFORMATION: oligonucleotide primer

<400> SEQUENCE: 51

gcgaacagca taataatcgc attgaatgga cggg                                34


<210> SEQ ID NO 52
<211> LENGTH: 26
<212> TYPE: DNA
<213> ORGANISM: Artificial
<220> FEATURE:
<223> OTHER INFORMATION: oligonucleotide primer

<400> SEQUENCE: 52

cagagtgaca acatcgagta tgtgtc                                         26


<210> SEQ ID NO 53
<211> LENGTH: 36
<212> TYPE: DNA
<213> ORGANISM: Artificial
<220> FEATURE:
<223> OTHER INFORMATION: oligonucleotide primer

<400> SEQUENCE: 53

cagagtgaca acttcgagat tgtgtcattc aagacc                              36


<210> SEQ ID NO 54
<211> LENGTH: 26
<212> TYPE: DNA
<213> ORGANISM: Artificial
<220> FEATURE:
<223> OTHER INFORMATION: oligonucleotide primer

<400> SEQUENCE: 54

caacccttc aagatcctgg ttccac                                          26
```

What is claimed is:

1. A modified polypeptide comprising a substitution of one or more amino acids selected from the group consisting of lysine, methionine, isoleucine, and tryptophan into SEQ ID NO: 1.

2. The modified polypeptide of claim 1, wherein said modified polypeptide is capable of accumulating in a biological expression system.

3. The modified polypeptide of claim 2, wherein the biological expression system is a seed.

4. The modified polypeptide of claim 1, wherein the substitution is of two or more of said amino acids.

5. The modified polypeptide of claim 1, wherein said polypeptide comprises greater than about a 0.25% (weight per weight) increase of any one of said amino acids, or any combination thereof, relative to SEQ ID NO; 1.

6. A recombinant nucleic acid molecule encoding a modified glycinin polypeptide comprising a substitution of one or more amino acids selected from the group consisting of threonine, isoleucine, tryptophan, valine, arginine, lysine, methionine, and histidine into SEQ ID NO: 1.

7. The recombinant nucleic acid molecule of claim 6, wherein said modified glycinin polypeptide is capable of accumulating in a cell.

8. The recombinant nucleic acid molecule of claim 7, further comprising, in the 5' to 3' direction, a heterologous promoter operably linked to said recombinant nucleic acid molecule.

9. A cell containing, in the 5' to 3' direction, a heterologous promoter operably linked to a recombinant nucleic acid molecule encoding a modified glycinin polypeptide comprising a substitution of one or more amino acids selected from the group consisting of threonine, isoleucine, tryptophan, valine, arginine, lysine, methionine, and histidine into SEQ ID NO: 1.

10. The cell of claim 9, wherein said modified glycinin polypeptide is capable of accumulating in a seed.

11. The cell according to claim 9, wherein said cell is selected from the group consisting of a bacterial cell, a mammalian cell, an insect cell, a plant cell, and a fungal cell.

* * * * *